United States Patent

Kawamura

(10) Patent No.: US 8,507,106 B2
(45) Date of Patent: Aug. 13, 2013

(54) BENZOPHENANTHRENE DERIVATIVE AND ORGANIC ELECTROLUMINESCENT DEVICE EMPLOYING THE SAME

(75) Inventor: Masahiro Kawamura, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 360 days.

(21) Appl. No.: 12/744,926

(22) PCT Filed: Nov. 25, 2008

(86) PCT No.: PCT/JP2008/071284
§ 371 (c)(1),
(2), (4) Date: Jul. 29, 2010

(87) PCT Pub. No.: WO2009/069566
PCT Pub. Date: Jun. 4, 2009

(65) Prior Publication Data
US 2010/0320452 A1  Dec. 23, 2010

(30) Foreign Application Priority Data
Nov. 29, 2007  (JP) .................. 2007-309072

(51) Int. Cl.
*H01L 51/54* (2006.01)
*C07C 13/48* (2006.01)
*C07C 25/18* (2006.01)
*C07C 211/43* (2006.01)

(52) U.S. Cl.
USPC ............ 428/690; 428/917; 585/26; 570/183; 564/427; 564/426; 313/504; 313/506

(58) Field of Classification Search
None
See application file for complete search history.

(56) References Cited

U.S. PATENT DOCUMENTS

| 5,935,721 | A | 8/1999 | Shi et al. |
| 2004/0076853 | A1 | 4/2004 | Jarikov |
| 2007/0155998 | A1 | 7/2007 | Saitoh et al. |
| 2008/0182129 | A1* | 7/2008 | Klubek et al. ............. 428/704 |
| 2012/0056165 | A1* | 3/2012 | Kawamura et al. ......... 257/40 |

FOREIGN PATENT DOCUMENTS

| JP | 2001-335516 | 12/2001 |
| JP | 2005-041843 | 2/2005 |
| JP | 2006-151844 | 6/2006 |
| JP | 2007-230951 | 9/2007 |
| WO | WO-2007/123256 A1 | 11/2007 |

OTHER PUBLICATIONS

International Preliminary Report on Patentability in PCT/JP2008/071284 dated Jun. 17, 2010.
International Search Report in PCT/JP2008/071284 dated Dec. 22, 2008.
Seliger, et al. "Chemical Production of excited states. Chemiluminescence of Carcinogenic Hydrocarbons Accompanying their Metabolic Hydroxylation and a Proposal for Common Active Site Geometries for Hydroxylation" Journal of Physical Chemistry, 1976, vol. 80, No. 20, pp. 2296-2306.

* cited by examiner

*Primary Examiner* — Dawn Garrett
(74) *Attorney, Agent, or Firm* — Foley & Lardner LLP

(57) ABSTRACT

A fused aromatic ring derivative shown by the following formula (1):

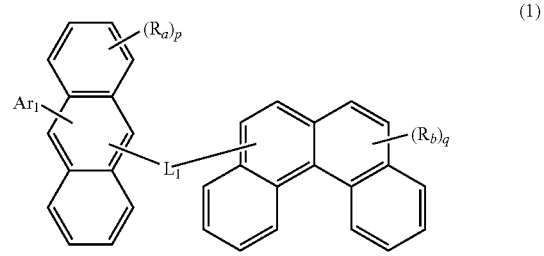

(1)

wherein $R_a$ and $R_b$ are independently a hydrogen atom or a substituent, p is an integer of 1 to 8 and q is an integer of 1 to 11, when p is 2 or more, plural $R_a$s may be independently the same or different and adjacent $R_a$s may form a ring, when q is 2 or more, plural $R_b$s may be independently the same or different, $L_1$ is a single bond, or a substituted or unsubstituted divalent linking group, and $Ar_1$ is a substituted or unsubstituted aryl group having 6 to 50 ring carbon atoms or a substituted or unsubstituted heteroaryl group having 5 to 50 ring atoms, provided that the substituent of $L_1$, the substituent of $Ar_1$, $R_a$ and $R_b$ contain no substituted or unsubstituted amino group.

18 Claims, 1 Drawing Sheet

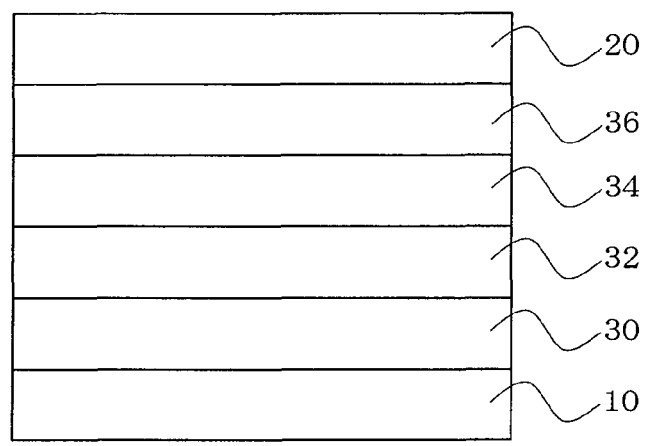

BENZOPHENANTHRENE DERIVATIVE AND ORGANIC ELECTROLUMINESCENT DEVICE EMPLOYING THE SAME

TECHNICAL FIELD

The invention relates to a novel fused aromatic ring derivative (benzophenanthrene derivative) which is useful as a material for an organic electroluminescence device, and an organic electroluminescence device using the same.

BACKGROUND ART

An organic electroluminescence device (hereinafter the term "electroluminescence" is often abbreviated as "EL") is a self-emission device utilizing the principle that a fluorescent compound emits light by the recombination energy of holes injected from an anode and electrons injected from a cathode when an electric field is impressed.

An organic EL device has made a remarkable progress. In addition, since an organic EL device has characteristics such as low voltage driving, high luminance, variety in emission wavelength, high response and capability of fabricating a thin and lightweight emitting device, its application to a wide range of fields is expected.

Emission materials used in an organic EL device have conventionally been studied actively since they influence largely the color of light emitted by a device or on emission life.

As the emission material, a chelate complex such as tris(8-quinolinolato)aluminum complex, a coumalin derivative, a tetraphenylbutadiene derivative, a bisstyrylarylene derivative and an oxadiazole derivative are known. By using such emission materials, emission in a visible range from blue to red can be obtained.

Use of a phosphorescent compound as an emission material for utilizing triplet energy for emission has been studied. For example, it is known that an organic EL device using an iridium complex as an emission material exhibits a high luminous efficiency.

An organic EL device using polyphenylene vinylene (PPV) as a conjugated polymer is known. In this device, PPV is applied and formed into a single film and this device is confirmed to emit light.

Patent Document 1 discloses an organic EL device using a layer containing 9,10-di-(2-naphthyl)anthracene derivative as an organic layer. Patent Documents 2 and 3 disclose an organic EL device using a layer containing a phenanthrene derivative as an emitting layer.

Patent Document 1: U.S. Pat. No. 5,935,721
Patent Document 2: U.S. Patent application publication No. 2004/076853
Patent Document 3: JP-A-2006-151844

An object of the invention is to provide an organic material which is suitable for use as a material of an organic EL device.

DISCLOSURE OF THE INVENTION

The inventor noticed a benzophenanthrene derivative as a material for an organic EL device and made intensive studies. As a result, the inventor has found that a benzophenanthrene derivative having a specific structure is effective for prolonging the lifetime, increasing the efficiency and lowering the voltage of an organic EL device. The invention has been made on this finding.

According to the invention, the following fused aromatic ring derivative or the like can be provided.

1. A fused aromatic ring derivative shown by the following formula (1):

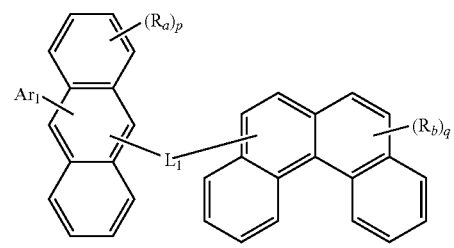

wherein $R_a$ and $R_b$ are independently a hydrogen atom or a substituent, p is an integer of 1 to 8 and q is an integer of 1 to 11, when p is 2 or more, plural $R_a$s may be independently the same or different and adjacent $R_a$s may form a ring, when q is 2 or more, plural $R_b$s may be independently the same or different, $L_1$ is a single bond, or a substituted or unsubstituted divalent linking group, and $Ar_1$ is a substituted or unsubstituted aryl group having 6 to 50 carbon atoms that form a ring (hereinafter abbreviated as "ring carbon atoms") or a substituted or unsubstituted heteroaryl group having 5 to 50 atoms that form a ring (hereinafter abbreviated as "ring atoms"), provided that the substituent of $L_1$, the substituent of $Ar_1$, $R_a$ and $R_b$ contain no substituted or unsubstituted amino group.

2. The fused aromatic ring derivative according to 1, which is shown by the following formula (2):

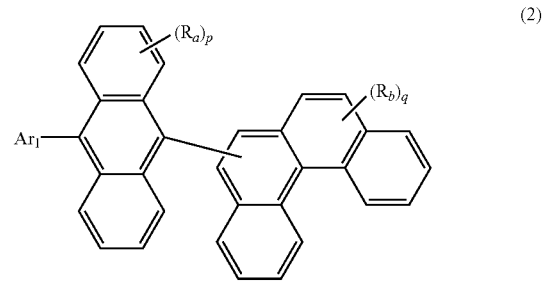

wherein $R_a$, $R_b$, $Ar_1$, p and q are the same as in the formula (1).

3. The fused aromatic ring derivative according to 1 or 2, wherein $Ar_1$ is a substituted or unsubstituted fused aromatic ring group having 10 to 20 ring carbon atoms.

4. The fused aromatic ring derivative according to 1, which is shown by the following formula (3):

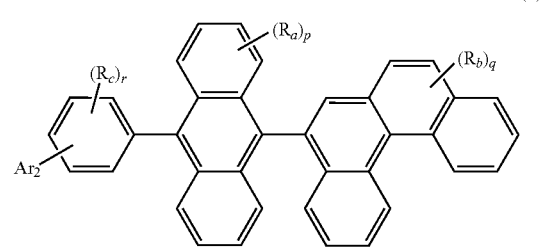

wherein $R_a$, $R_b$, p and q are the same as in the formula (1), $R_c$ is independently a halogen atom or a substituent, r is an integer of 1 to 4, when r is 2 or more, plural $R_c$s may be independently the same or different and adjacent $R_c$s may form a ring, and $Ar_2$ is a substituted or unsubstituted aryl group having 6 to 50 ring carbon atoms, provided that the substituent of $Ar_2$ and $R_c$ contain no substituted or unsubstituted amino group.

5. The fused aromatic ring derivative according to 4, wherein $Ar_2$ is a substituted or unsubstituted fused aromatic ring group having 10 to 20 ring carbon atoms.

6. The fused aromatic ring derivative according to 1, which is shown by the following formula (4):

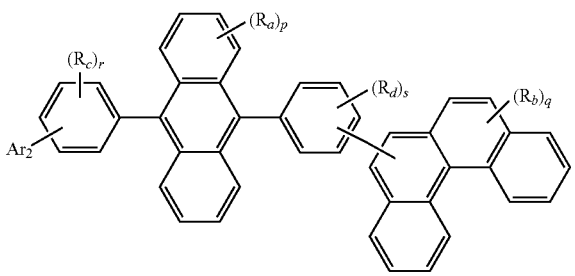

(4)

wherein $R_a$, $R_b$, p and q are the same as in the formula (1), $R_c$ and $R_d$ are independently a hydrogen atom or a substituent, r is an integer of 1 to 4 and s is an integer of 1 to 4, when r is two or more, plural $R_c$s may be independently the same or different, when s is two or more, plural $R_d$s may be independently the same or different, and $Ar_2$ is a substituted or unsubstituted aryl group having 6 to 50 ring carbon atoms, provided that the substituent of $Ar_2$, $R_c$ and $R_d$ contain no substituted or unsubstituted amino group.

7. The fused aromatic ring derivative according to 6, wherein $Ar_2$ is a substituted or unsubstituted fused aromatic ring group having 10 to 20 ring carbon atoms.

8. The fused aromatic ring derivative according to 1, which is shown by the following formula (5):

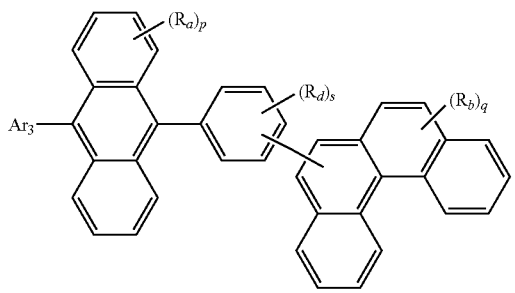

(5)

wherein $R_a$, $R_b$, p and q are the same as in the formula (1), $R_d$ is independently a hydrogen atom or a substituent, s is an integer of 1 to 4, when s is two or more, plural $R_d$s may be independently the same or different, and $Ar_3$ is a substituted or unsubstituted fused aromatic ring group having 10 to 50 ring carbon atoms, provided that the substituent of $Ar_3$ and $R_d$ contain no substituted or unsubstituted amino group.

9. The fused aromatic ring derivative according to 8, wherein $Ar_3$ is a substituted or unsubstituted naphthyl group.

10. A material for an organic electroluminescence device comprising the fused aromatic ring derivative according to any of 1 to 9.

11. The material for an organic electroluminescence device according to 10, which is an emitting material.

12. An organic electroluminescence device comprising:

an anode, a cathode, and one or more organic thin film layers comprising an emitting layer between the anode and the cathode, wherein at least one of the organic thin film layers comprises the fused aromatic ring derivative according to any of 1 to 9.

13. The organic electroluminescence device according to 12, wherein the emitting layer comprises the fused aromatic ring derivative.

14. The organic electroluminescence device according to 13, wherein the fused aromatic ring derivative is a host material.

15. The organic electroluminescence device according to any of 12 to 14, wherein the emitting layer further comprises one of a fluorescent dopant and a phosphorescent dopant.

16. The organic electroluminescence device according to 15, wherein the fluorescent dopant is an aryl amine compound.

17. The organic electroluminescence device according to 15, wherein the fluorescent dopant is a styryl amine compound.

According to the invention, it is possible to provide a fused aromatic ring derivative suitable as a material for an organic EL device.

The organic EL device using the fused aromatic ring derivative of the invention has a long lifetime and a high efficiency, and is capable of being driven at a low voltage.

BRIEF DESCRIPTION OF THE DRAWINGS

FIG. 1 is a schematic cross-sectional view of the organic EL device according to one embodiment of the invention.

BEST MODE FOR CARRYING OUT THE INVENTION

The fused aromatic ring derivative of the invention will be described below in detail.

The fused aromatic ring derivative of the invention is a compound shown by the following formula (1), preferably one of the compounds shown by the following formulas (2) to (5):

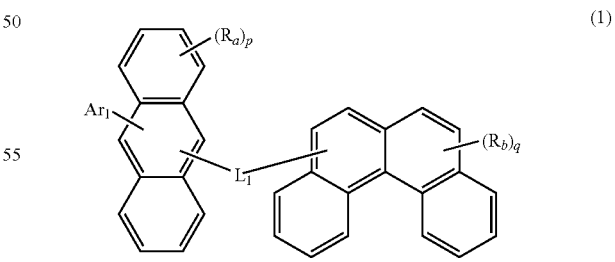

(1)

wherein $R_a$ and $R_b$ are independently a hydrogen atom or a substituent, p is an integer of 1 to 8 and q is an integer of 1 to 11, when p is 2 or more, plural $R_a$s may be independently the same or different and adjacent $R_a$s may form a ring, when q is 2 or more, plural $R_b$s may be independently the same or different, $L_1$ is a single bond, or a substituted or unsubstituted divalent linking group, and $Ar_1$ is a substituted or unsubstituted aryl group having 6 to 50 ring carbon atoms or a substituted or unsubstituted heteroaryl group having 5 to 50 ring atoms, provided that the substituent of $L_1$, the substituent of $Ar_1$, $R_a$ and $R_b$ contain no substituted or unsubstituted amino group.

(2)

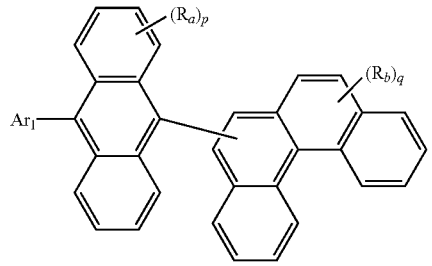

wherein $R_a$, $R_b$, $Ar_1$, p and q are the same as in the formula (1).

(3)

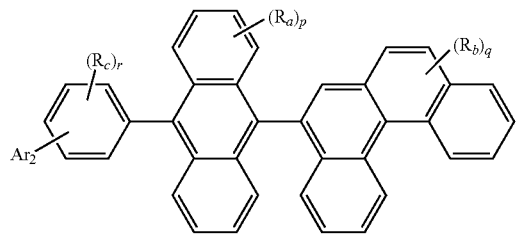

wherein $R_a$, $R_b$, p and q are the same as in the formula (1), $R_c$ is independently a halogen atom or a substituent, r is an integer of 1 to 4, when r is 2 or more, plural $R_c$s may be independently the same or different, and $Ar_2$ is a substituted or unsubstituted aryl group having 6 to 50 ring carbon atoms, provided that the substituent of $Ar_2$ and $R_c$ contain no substituted or unsubstituted amino group.

(4)

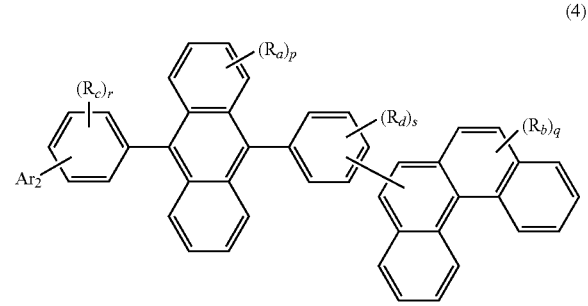

wherein $R_a$, $R_b$, p and q are the same as in the formula (1), $R_c$ and $R_d$ are independently a hydrogen atom or a substituent, r is an integer of 1 to 4 and s is an integer of 1 to 4, when r is two or more, plural $R_c$s may be independently the same or different, when s is two or more, plural $R_d$s may be independently the same or different, and $Ar_2$ is a substituted or unsubstituted aryl group having 6 to 50 ring carbon atoms, provided that the substituent of $Ar_2$, $R_c$ and $R_d$ contain no substituted or unsubstituted amino group.

(5)

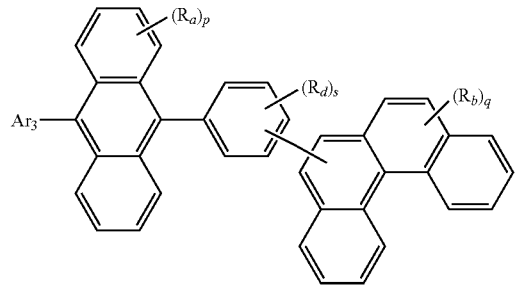

wherein $R_a$, $R_b$, p and q are the same as in the formula (1), $R_d$ is independently a hydrogen atom or a substituent, s is an integer of 1 to 4, when s is two or more, plural $R_d$s may be independently the same or different, and $Ar_3$ is a substituted or unsubstituted fused aromatic ring group having 10 to 50 ring carbon atoms, provided that the substituent of $Ar_3$ and $R_d$ contain no substituted or unsubstituted amino group.

Examples of the substituent which contains no substituted or unsubstituted amino group shown by $R_a$, $R_b$, $R_c$ and $R_d$ include an alkyl group (one having preferably 1 to 20, more preferably 1 to 12 and particularly preferably 1 to 8 carbon atoms, the specific examples of which include methyl, ethyl, isopropyl, t-butyl, n-octyl, n-decyl, n-hexadecyl, cyclopropyl, cyclopentyl and cyclohexyl), an alkenyl group (one having preferably 2 to 20, more preferably 2 to 12 and particularly preferably 2 to 8 carbon atoms, the specific examples of which include vinyl, allyl, 2-butenyl and 3-pentenyl), an alkynyl group (one having preferably 2 to 20, more preferably 2 to 12 and particularly preferably 2 to 8 carbon atoms, the specific examples of which include propynyl and 3-pentynyl), a substituted or unsubstituted aryl group (one having preferably 6 to 20 and particularly preferably 6 to 14 carbon atoms, the specific examples of which include phenyl, naphthyl, phenanthryl and fluorenyl), an aryl group (one having preferably 6 to 20 and particularly preferably 6 to 14 carbon atoms, provided that one contains no anthracene skelton, the specific examples of which include phenyl, naphthyl and phenanthryl), a heteroaryl group (one having preferably 1 to 30 and more preferably 1 to 12 carbon atoms, the specific examples of which include furyl, thienyl, benzoxazolyl, benzothiazolyl, benzofuranyl, dibenzofuranyl, benzothiopheny and dibenzothiophenyl), an alkoxy group (one having preferably 1 to 20, more preferably 1 to 12 and particularly preferably 1 to 8 carbon atoms, the specific examples of which include methoxy, ethoxy and buthoxy), an aryloxy group (one having preferably 6 to 20, more preferably 6 to 16 and particularly preferably 6 to 12 carbon atoms, the specific examples of which include phenyloxy and 2-naphthyloxy), an acyl group (one having preferably 1 to 20, more preferably 1 to 16 and particularly preferably 1 to 12 carbon atoms, the specific examples of which include acetyl, benzoyl, formyl and pivaloyl), an alkoxycarbonyl group (one having preferably 2 to 20, more preferably 2 to 16 and particularly preferably 2 to 12 carbon atoms, the specific examples of which include methoxycarbonyl and ethoxycarbonyl), an aryloxycarbonyl group (one having preferably 7 to 20, more preferably 7 to 16 and particularly preferably 7 to 10 carbon atoms, the specific examples of which include phenyloxycarbonyl), an acyloxy group (one having preferably 2 to 20, more preferably 2 to 16 and particularly preferably 2 to 10 carbon atoms, the specific examples of which include acetoxy and benzoyloxy), an alkylthio group (one having preferably 1 to 20, more preferably 1 to 16 and particularly preferably 1 to 12 carbon atoms, the specific examples of which include methylthio and ethylthio), an arylthio group (one having preferably 6 to 20, more preferably 6 to 16 and particularly preferably 6 to 12 carbon atoms, the specific examples of which include phenylthio), a substituted or unsubstituted sulfonyl group (one having preferably 1 to 20, more preferably 1 to 16 and particularly preferably 1 to 12 carbon atoms, the specific examples of which include mesyl and tosyl), a substituted or unsubstituted sulfinyl group (one having preferably 1 to 20, more preferably 1 to 16 and particularly preferably 1 to 12 carbon atoms, the specific examples of which include methanesulfinyl and benezenesulfinyl), a hydroxyl group, a mercapto group, a halogen atom (for example, a fluorine atom, a chlorine atom, a bromine atom and an iodine atom), a cyano group, a sulfo group, a carboxyl group, a sulfino group, a heterocyclic group (one having preferably 1 to 30 and more preferably 1 to 12 carbon atoms and containing, as the hetero atom, an oxygen atom and a sulfur atom, for example, the specific examples of which include furyl, thienyl, benzoxazolyl and benzothiazolyl), and a silyl group (one having preferably 3 to 40, more preferably 3 to 30 and particularly preferably 3 to 24 carbon atoms, the examples of which include trimethylsilyl and triphenylsilyl). These substituents may be further substituted. If there are two or more substituents, these substituents may be the same or different. If possible, they may be combined each other to form a ring.

In the case where the above-mentioned substituents further have a substituent, the same substituents as those exemplified for $R_a$ to $R_d$ in the formula (1) can be given. Hereinafter, the same applies for the case where each group of formulas (1) to (5) has a substituent.

In the invention, among the above-mentioned substituents, an alkyl group, an alkenyl group, an aryl group, a dibenzofuranylaryl group, and dibenzothiophenylaryl group are preferable.

Examples of the substituted or unsubstituted divalent linking group shown by $L_1$ include a substituted or unsubstituted arylene having 6 to 50 ring carbon atoms. Specific examples include a divalent group obtained by removing one hydrogen atom from the aryl groups below.

A phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group and the like.

The substituent of the above-mentioned linking group contains no substituted or unsubstituted amino group.

As a preferable $L_1$, for example, a single bond, or linking groups described below can be given.

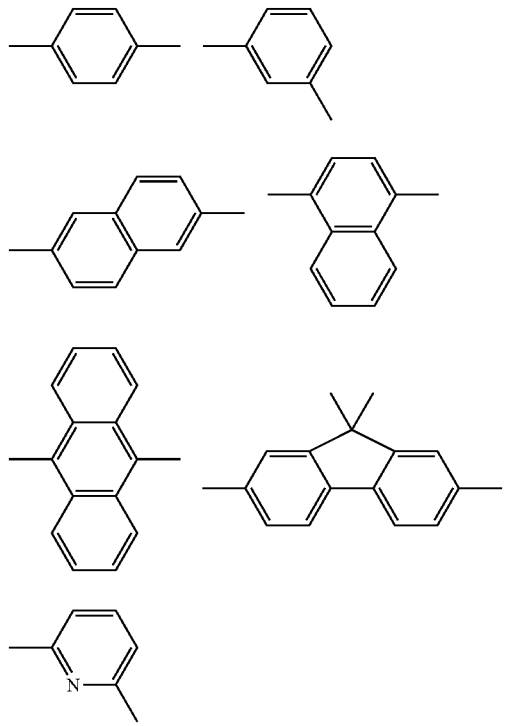

As a substituted or unsubstituted aryl group having 6 to 50 ring carbon atoms shown by $Ar_1$ and $Ar_2$, a substituted or unsubstituted aryl group having 6 to 20 ring carbon atoms is preferable, and for example, a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group and benzophenathryl group shown bellow can be given.

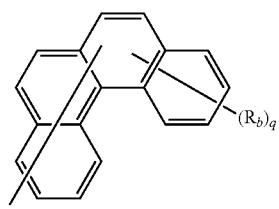

wherein $R_b$ and q are the same as in the formula (1).

The substituent of the aryl group having 6 to 50 ring carbon atoms contains no substituted or unsubstituted amino group.

$Ar_1$ and $Ar_2$ are preferably a substituted or unsubstituted fused aromatic ring group having 10 to 20 ring carbon atoms.

Specific Examples of the substituted or unsubstituted fused aromatic ring group having 10 to 20 ring carbon atoms include a 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group and 4-methyl-1-anthryl group.

Examples of the substituted or unsubstituted fused aromatic ring group having 10 to 50 ring carbon atoms shown by $Ar_a$ include 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 3-methyl-2-naphthyl group, 4-methyl-1-naphthyl group and 4-methyl-1-anthryl group. The substituted or unsubstituted naphthyl groups are preferable. The unsubstituted fused-aromatic ring groups having 10 to 20 ring carbon atoms are also preferable.

The substituent of the fused aromatic ring group having 10 to 50 ring carbon atoms contains no substituted or unsubstituted amino group.

Specific Examples of the fused aromatic ring derivative of the invention are shown below.

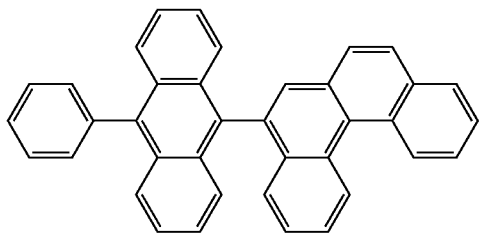

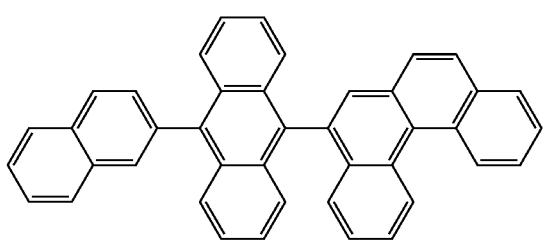

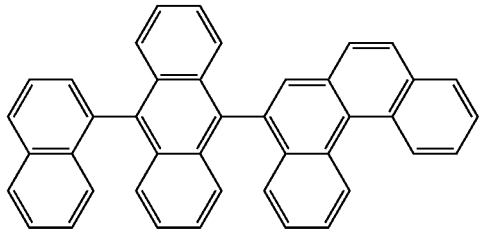

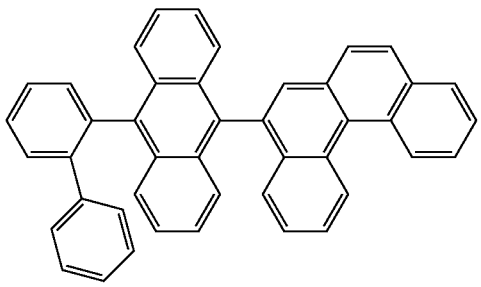

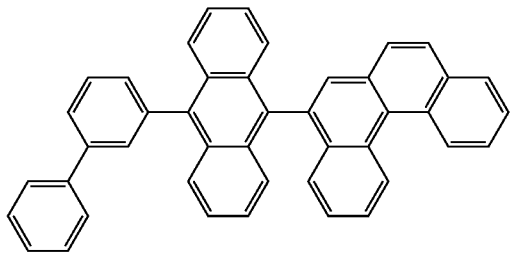

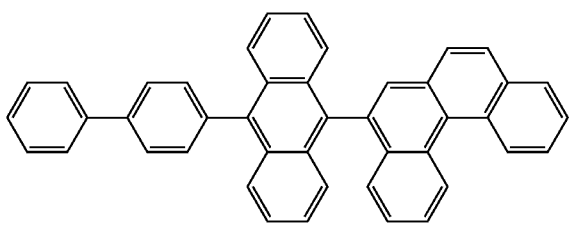

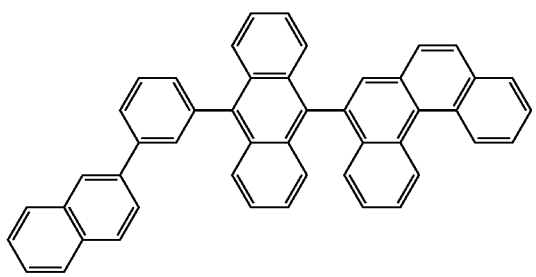

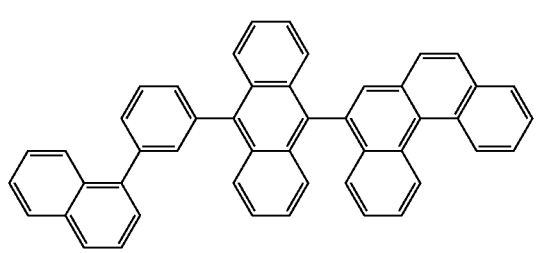

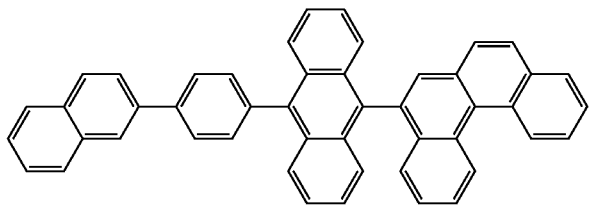

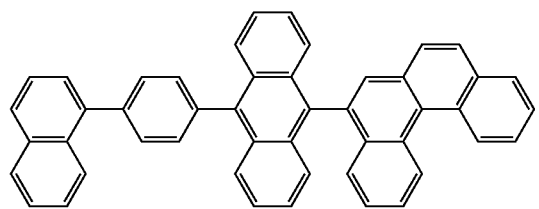

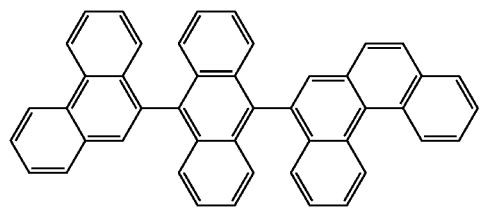
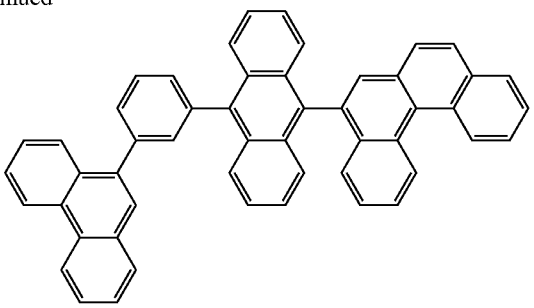
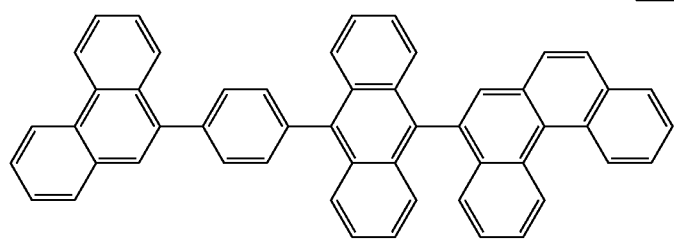
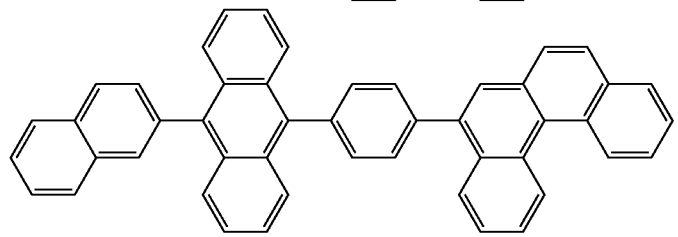
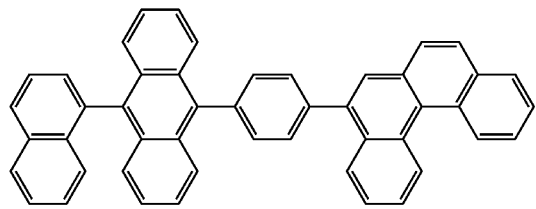
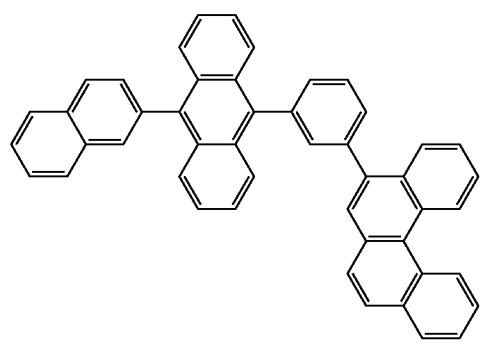
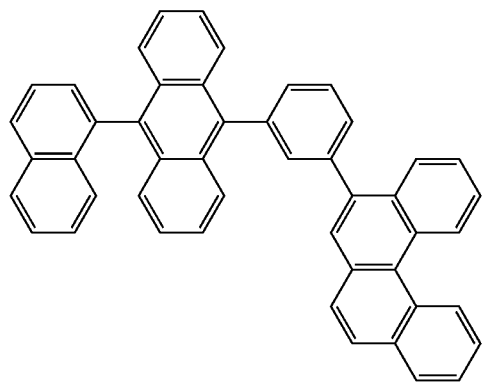
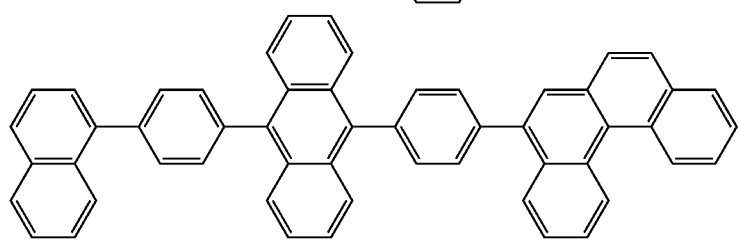

-continued
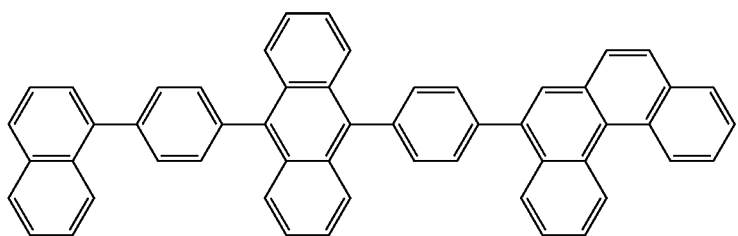
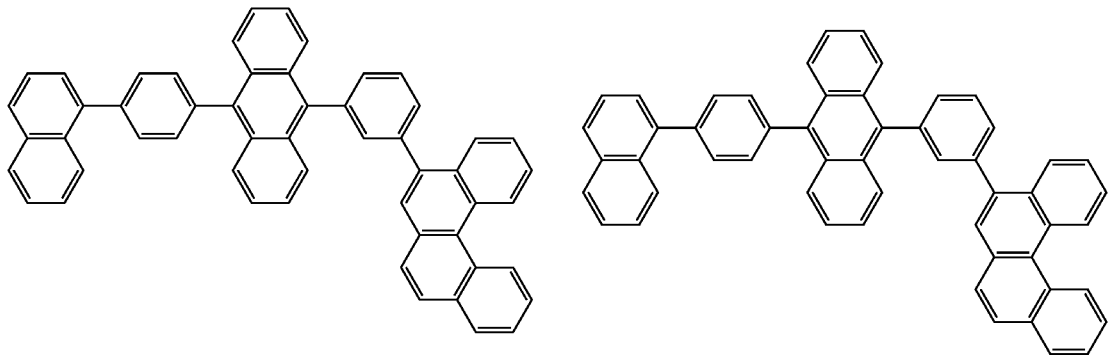
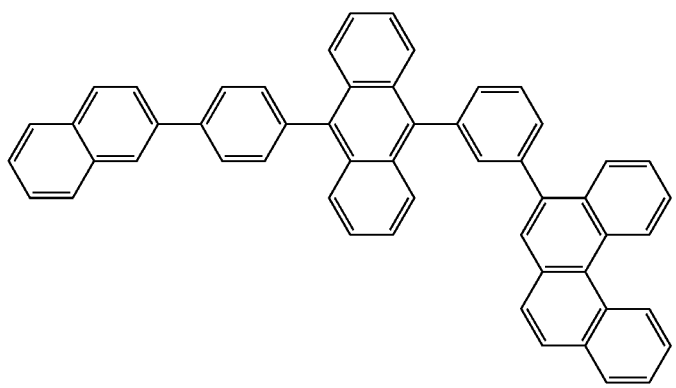
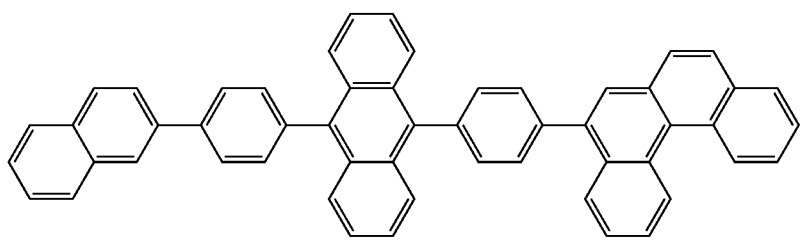
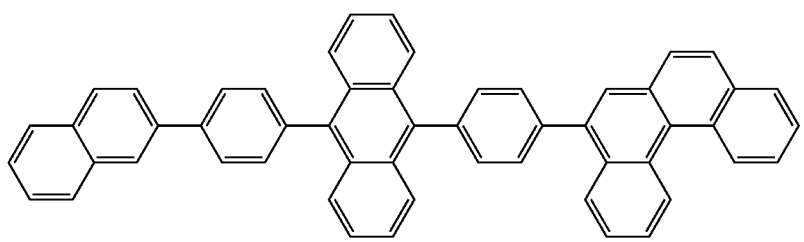

-continued
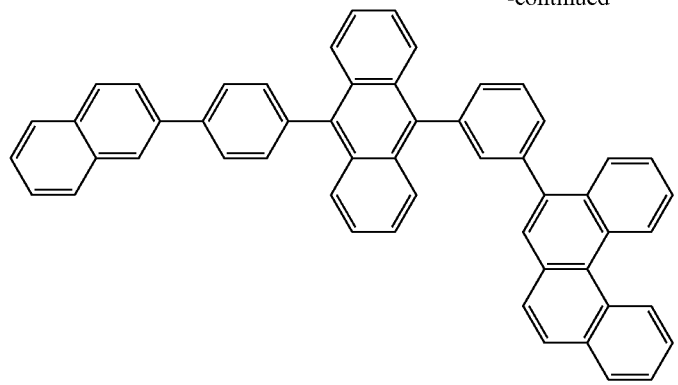
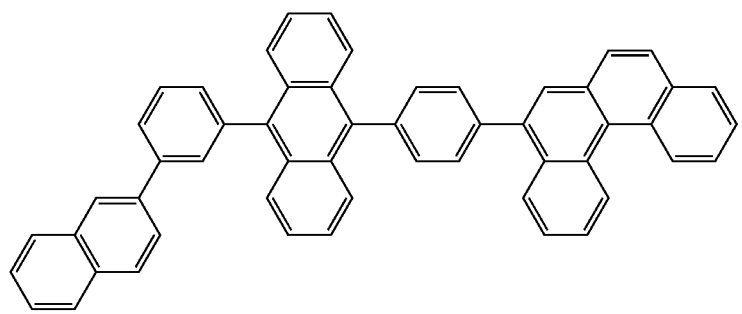
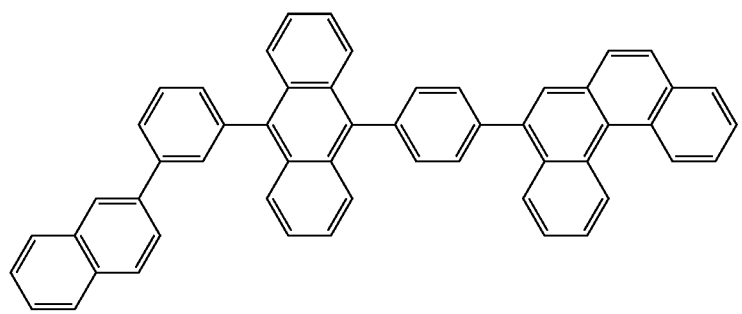
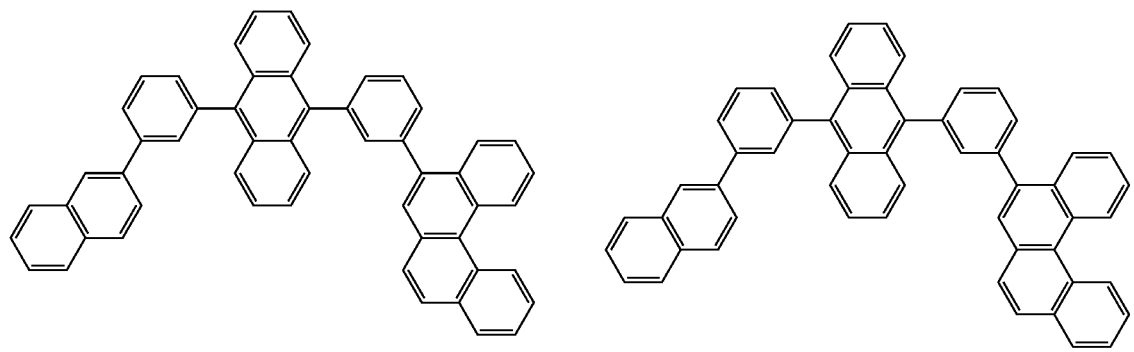
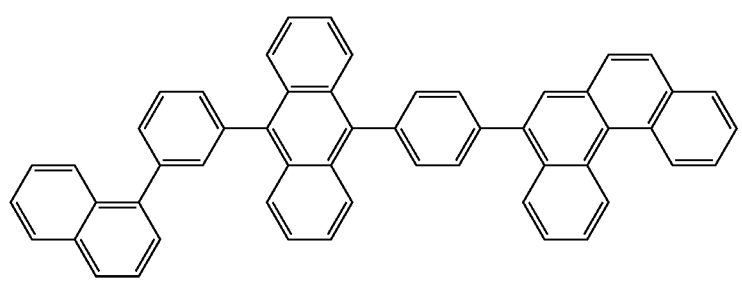

-continued
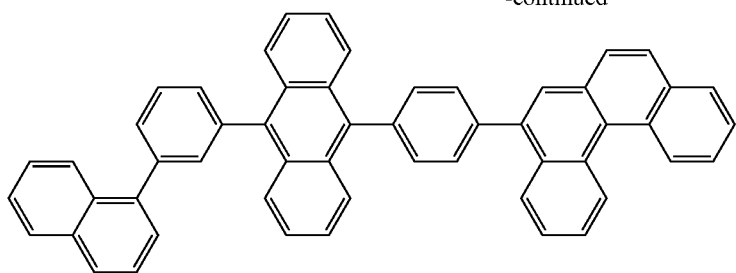
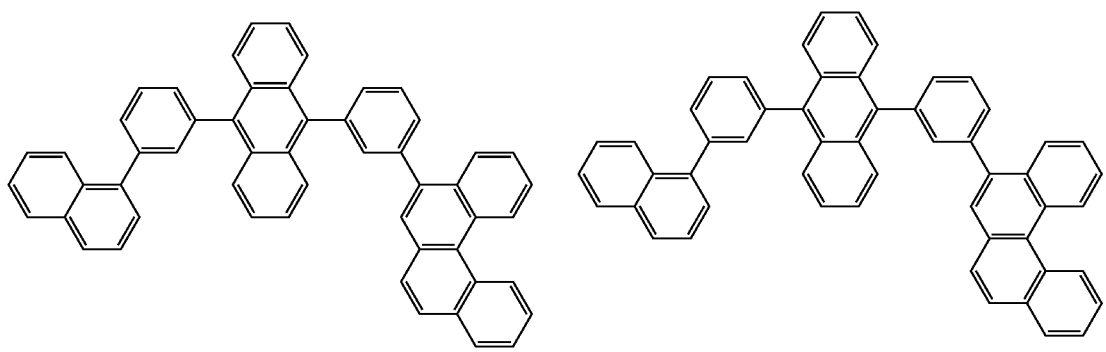
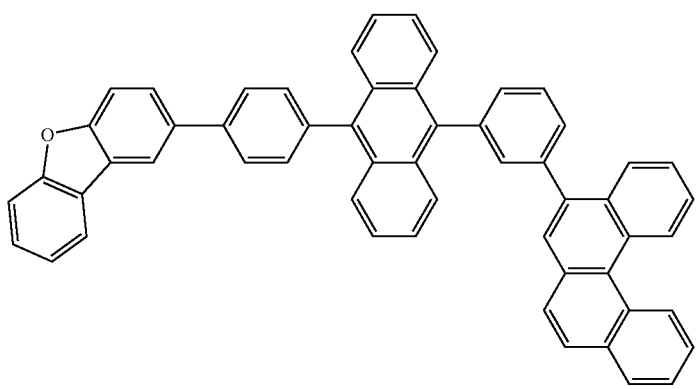
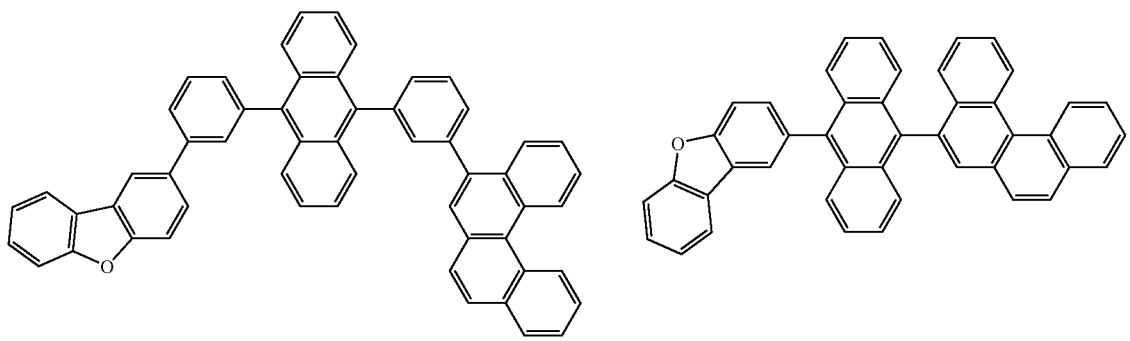
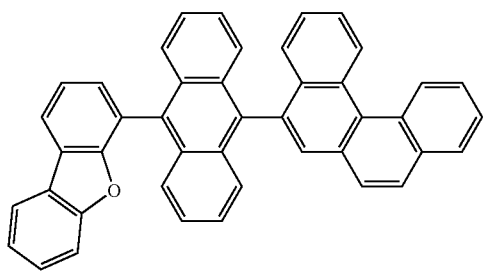
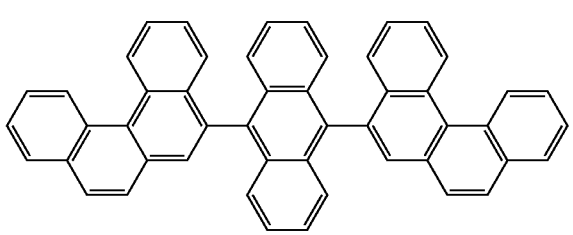

-continued
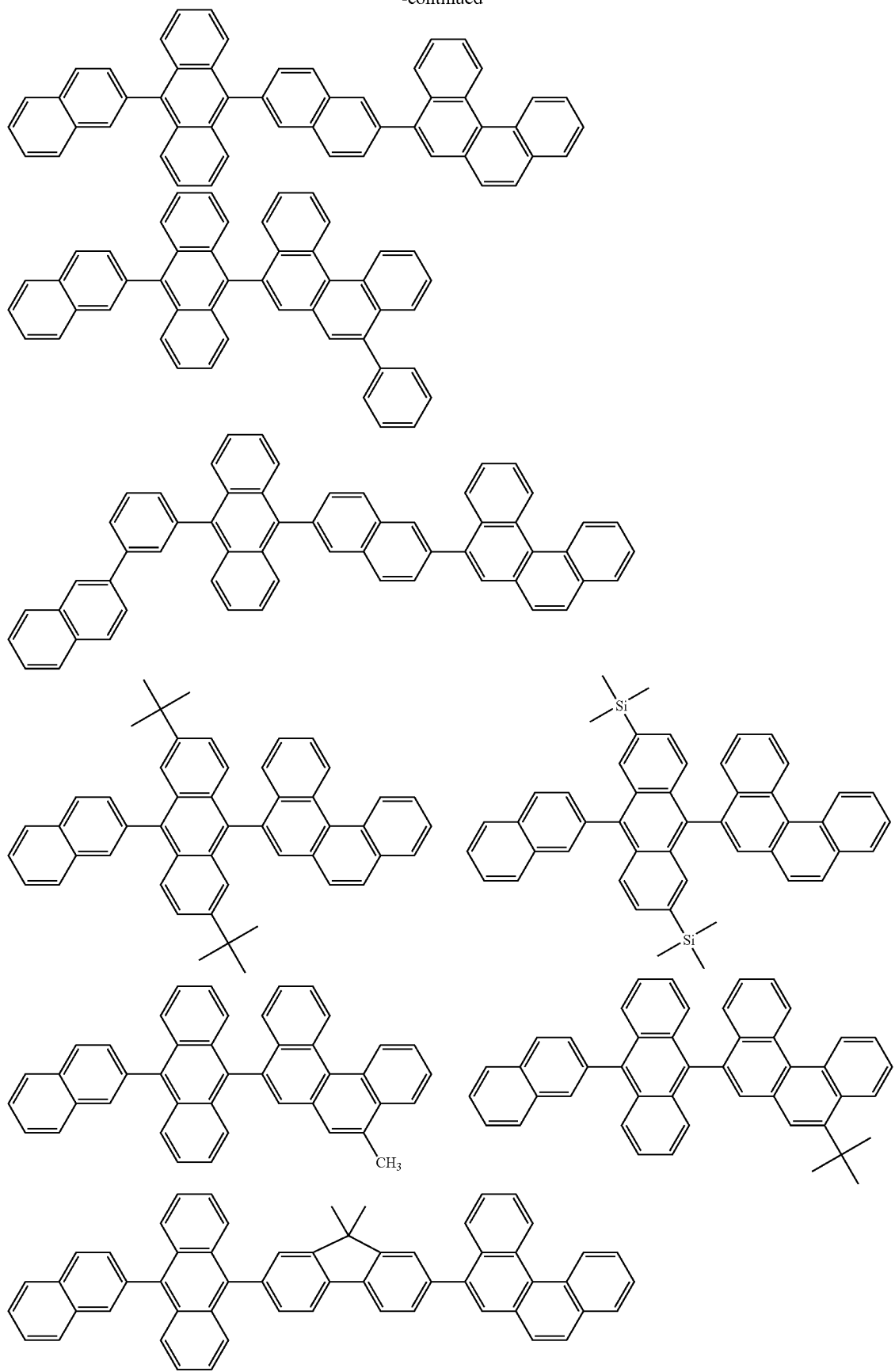

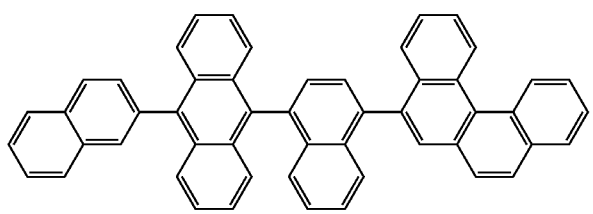
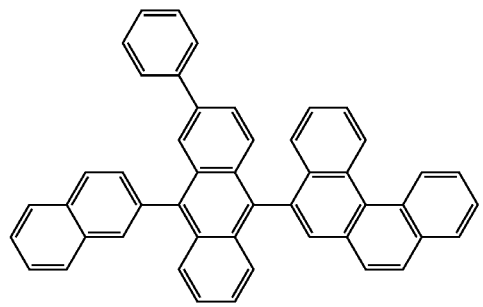
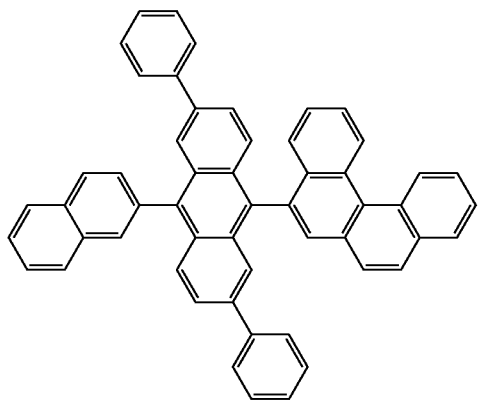
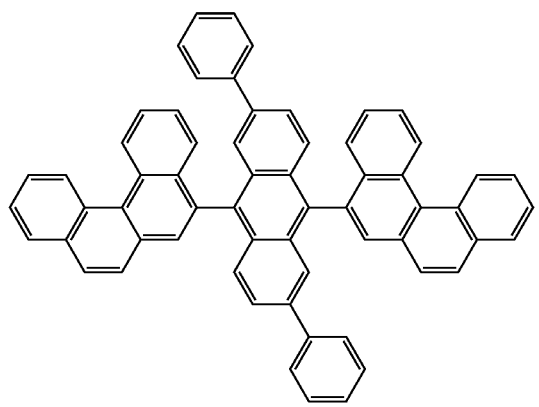
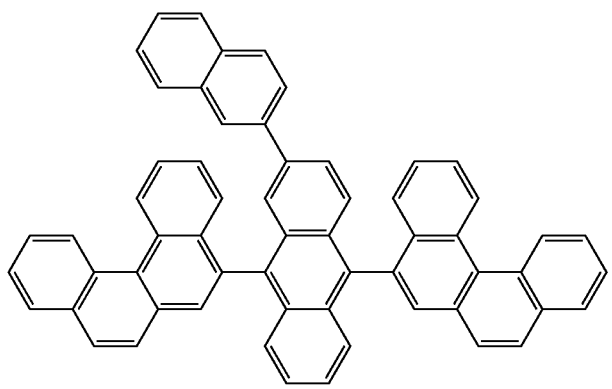
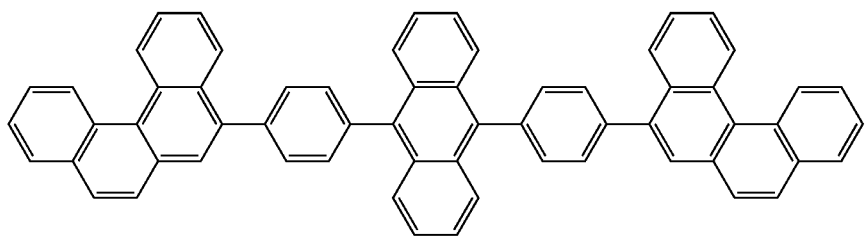
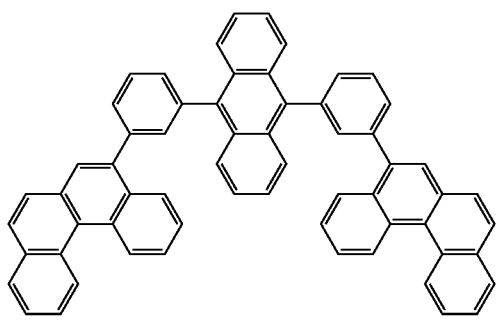
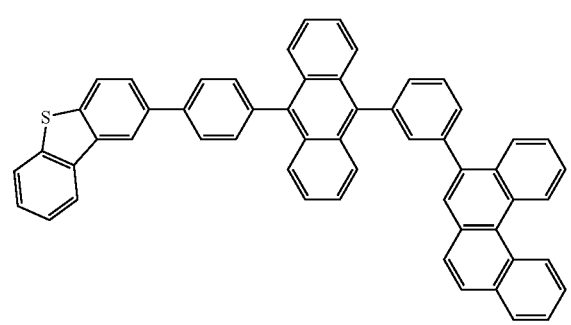

-continued
23
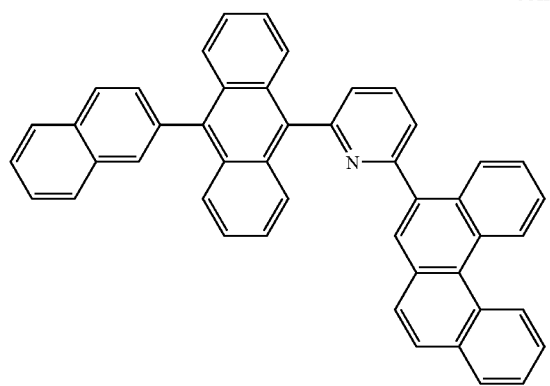
24
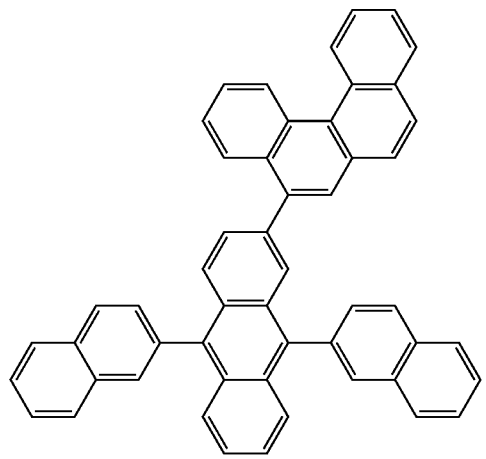
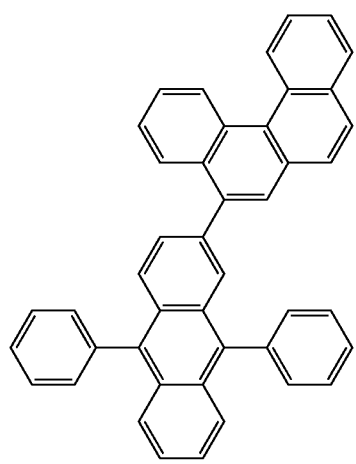
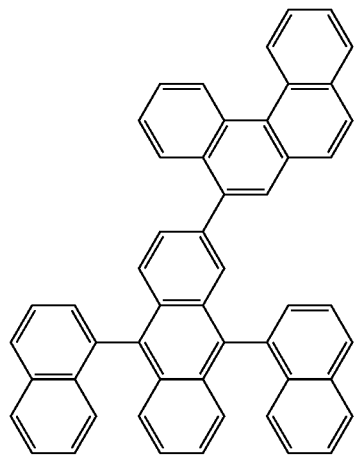
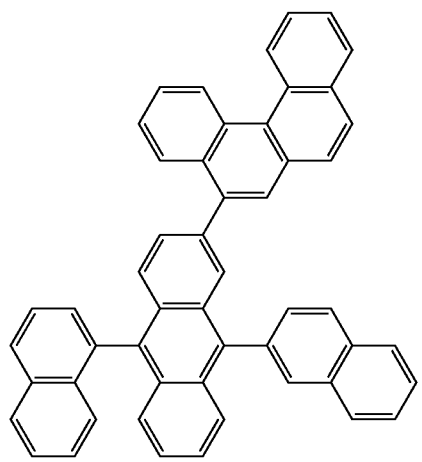
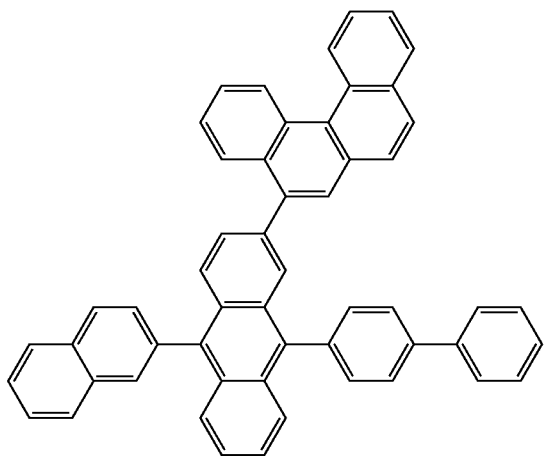

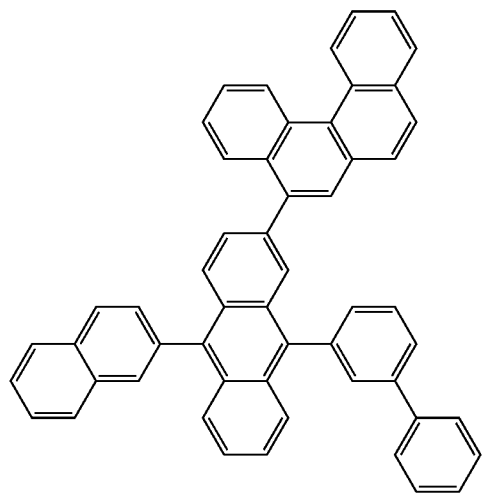
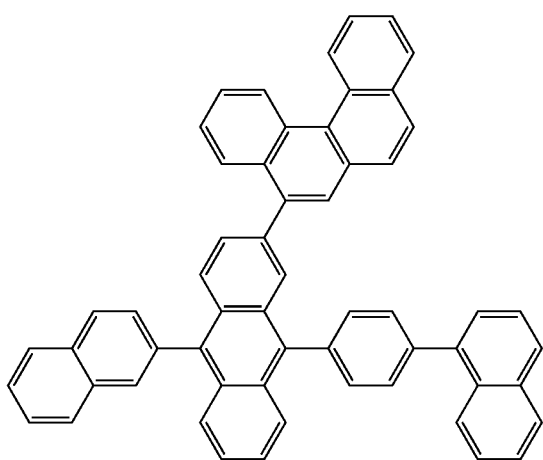
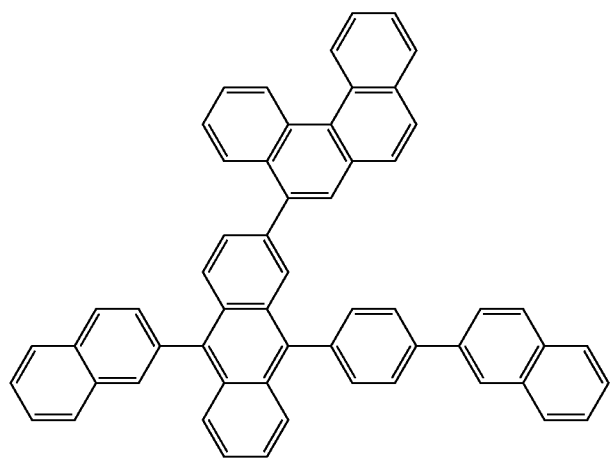
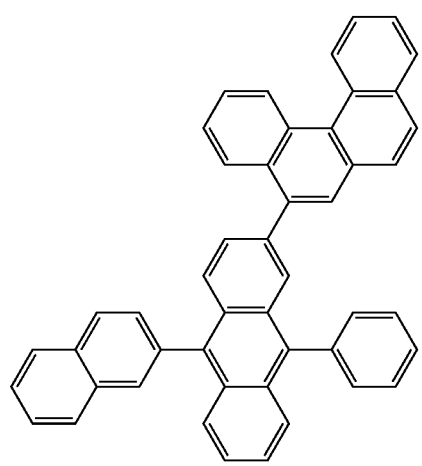
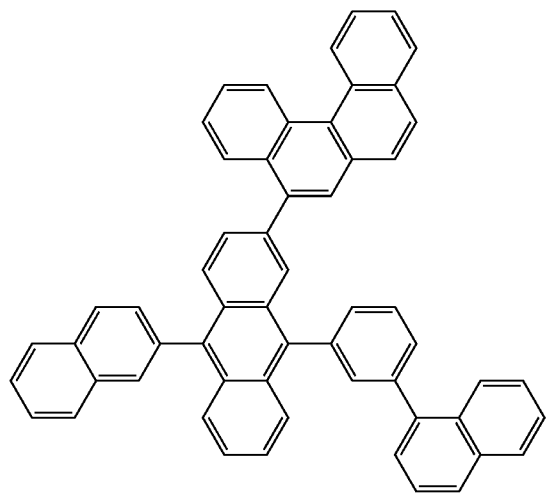
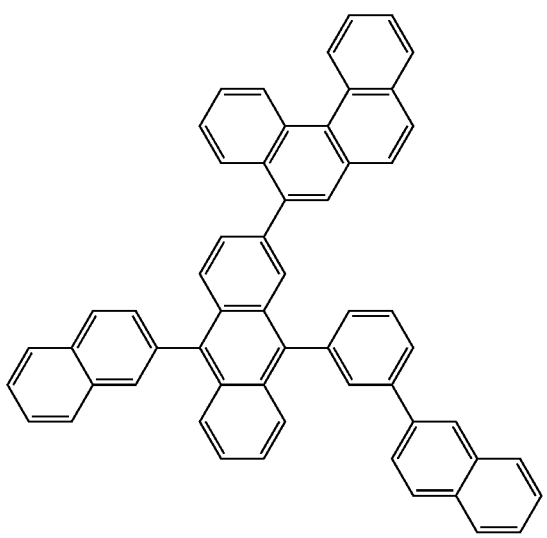

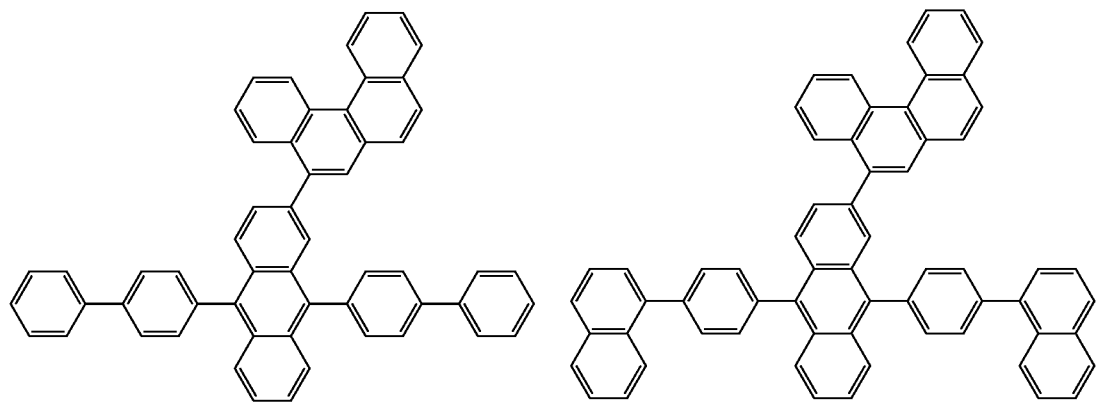
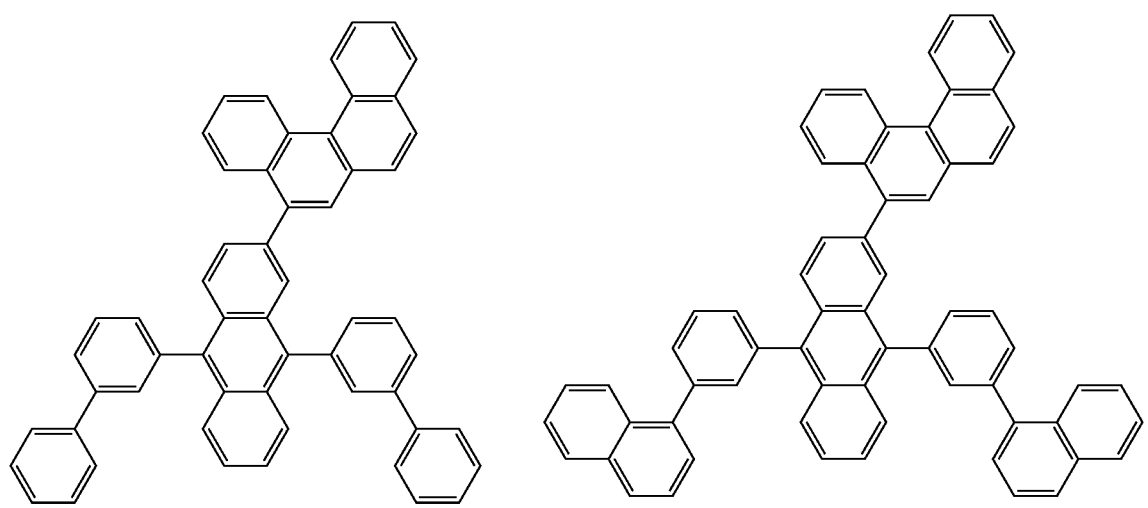
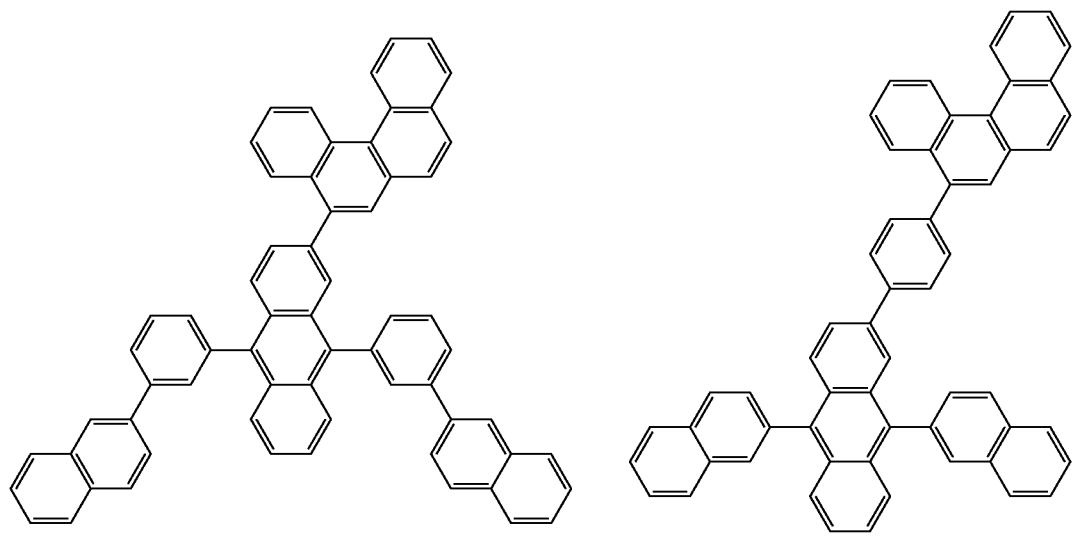

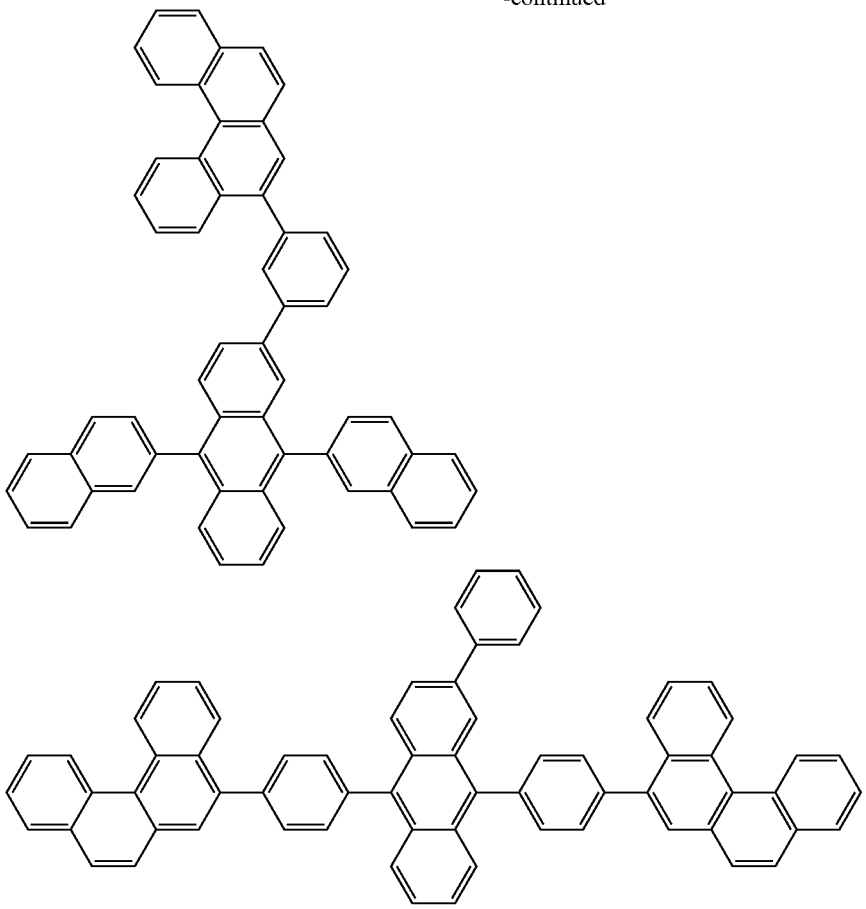

The fused aromatic ring derivative of the invention can be prepared, for example, by synthesis of a brominated benzophenanthrene derivative and then reaction of the resulting derivative with a boronic acid compound of an anthracene derivative.

The above-mentioned anthracene and benzophenanthrene are the following compounds.

anthracene

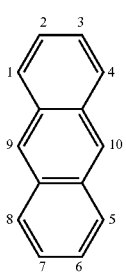

benzophenanthrene

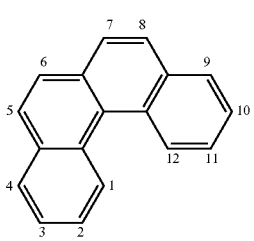

The fused aromatic ring derivative of the invention can be preferably used as a material for an organic EL device, in particular, as the emitting material thereof.

The organic EL device of the invention comprises an anode, a cathode and one or more organic thin layers comprising an emitting layer between the anode and the cathode, and at least one of the organic thin layers comprise the above-mentioned compound of the invention.

Representative configurations of the organic EL device of the invention can be given below.

(1) Anode/emitting layer/cathode
(2) Anode/hole-injecting layer/emitting layer/cathode
(3) Anode/emitting layer/electron-injecting layer/cathode
(4) Anode/hole-injecting layer/emitting layer/electron-injecting layer/cathode
(5) Anode/organic semiconductor layer/emitting layer/cathode
(6) Anode/organic semiconductor layer/electron-barrier layer/emitting layer/cathode
(7) Anode/organic semiconductor layer/emitting layer/adhesion-improving layer/cathode
(8) Anode/hole-injecting layer/hole-transporting layer/emitting layer/electron-injecting layer/cathode
(9) Anode/insulating layer/emitting layer/insulating layer/cathode
(10) Anode/inorganic semiconductor layer/insulating layer/emitting layer/insulating layer/cathode
(11) Anode/organic semiconductor layer/insulating layer/emitting layer/insulating layer/cathode
(12) Anode/insulating layer/hole-injecting layer/hole-transporting layer/emitting layer/insulating layer/cathode
(13) Anode/insulating layer/hole-injecting layer/hole-transporting layer/emitting layer/electron-injecting layer/cathode The representative examples of the configuration of the organic EL device of the invention are, however, not limited to the above. Of these, the configuration (8) is preferable.

The configuration (8) is shown in FIG. 1. This organic EL device comprises an anode 10, a cathode 20, and a hole-injecting layer 30, a hole-transporting layer 32, an emitting layer 34 and an electron-injecting layer 36 between the anode and the cathode. The hole-injecting layer 30, the hole-transporting layer 32, the emitting layer 34 and the electron-injecting layer 36 correspond to the plurality of organic thin film layers. At least one of these organic thin film layers 30, 32, 34 and 36 comprises the compound of the invention.

In the organic EL device of the invention, although the compound of the invention may be used in any of the above-mentioned organic thin film layers, it is preferred that the compound of the invention be used in the emitting layer. In each of the organic thin film layers, the compound of the invention may be used either singly or in mixture with other compounds. In the device of the invention, it is preferred that the emitting layer contain the compound of the invention as a host material and contain at least one of a fluorescent dopant and a phosphorescent dopant.

In the invention, it is preferred that the emitting layer consist essentially of the compound of the invention and the above-mentioned dopant.

The content of the compound of the invention in the organic thin film layers is preferably 30 to 100 mol %.

Each member of the organic EL device will be explained below.

The organic EL device is normally formed on a substrate. The substrate supports the organic EL device. It is preferable to use a smooth substrate. If light is outcoupled through the substrate, it is preferred that the substrate be a transparent substrate with a transmission to visible rays with a wavelength of 400 to 700 nm of 50% or more.

As such transparent substrate, a glass plate, a synthetic resin plate or the like are preferably used. Examples of the glass plate include plates of soda-lime glass, barium/strontium-containing glass, lead glass, aluminosilicate glass, borosilicate glass, barium borosilicate glass, quartz, or the like. Examples of the synthetic resin plates include plates of a polycarbonate resin, an acrylic resin, a polyethylene terephthalate resin, a polyether sulfide resin, a polysulfone resin, or the like.

It is effective that the anode injects holes to the hole-injecting layer, the hole-transporting layer or the emitting layer and has a work function of 4.5 eV or more. Specific examples of the anode material include indium tin oxide (ITO), a mixture of indium oxide and zinc oxide, a mixture of ITO and cerium oxide, a mixture of IZO and cerium oxide, a mixture of indium oxide and cerium oxide, a mixture of zinc oxide and aluminum oxide (AZO), tin oxide (NESA), gold, silver, platinum and copper.

The anode can be formed from these electrode materials by a vapor deposition method, a sputtering method or the like.

In the case where emission from the emitting layer is outcoupled through the anode, the transmittance of the anode to the emission is preferably more than 10%. The sheet resistance of the anode is preferably several hundred Ω/□ or less. The film thickness of the anode, which varies depending upon the material thereof, is usually from 10 nm to 1 μm, preferably from 10 to 200 nm.

The emitting layer has the following functions.
(i) Injection function: function of allowing injection of holes from the anode or hole-injecting layer and injection of electrons from the cathode or electron-injecting layer upon application of an electric field
(ii) Transporting function: function of moving injected carriers (electrons and holes) due to the force of an electric field
(iii) Emission function: function of recombining electrons and holes to emit light As the method of forming the emitting layer, a known method such as deposition, spin coating, or an LB method may be applied. It is preferable that the emitting layer be a molecular deposition film. The molecular deposition film is a film formed by deposition of a material compound in a gas phase, or by solidification of a material compound in the form of a solution or in a liquid phase. The molecular deposition film can be usually distinguished from a thin film (molecular accumulation film) formed using the LB method by the difference in aggregation structure or higher order structure or the difference in function due to the difference in structure.

The emitting layer may also be formed by dissolving a binder such as a resin and a material compound in a solvent to obtain a solution, and forming a thin film from the solution by spin coating or the like.

As mentioned above, it is preferred that the emitting layer contain the compound of the invention as a host material. The emitting layer may contain, in addition to the compound of the invention, host materials given below.

Specific examples of the host material which can be used in the emitting layer include compounds shown by the following formulas (i) to (ix):
Asymmetrical anthracene represented by the following formula (1):

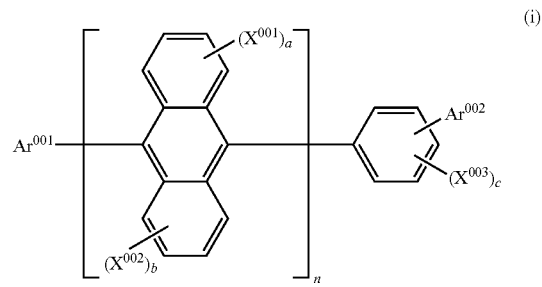

wherein $Ar^{001}$ is a substituted or unsubstituted fused aromatic group having 10 to 50 (preferably 10 to 30, more preferably 0.10 to 20) ring carbon atoms, $Ar^{002}$ is a substituted or unsubstituted aromatic group having 6 to 50 (preferably 6 to 20, more preferably 6 to 14) ring carbon atoms, $X^{001}$ to $X^{003}$ are independently a substituted or unsubstituted aromatic group having 6 to 50 (preferably 6 to 20, more preferably 6 to 14) ring carbon atoms, a substituted or unsubstituted aromatic heterocyclic group having 5 to 50 (preferably 5 to 20) ring atoms, a substituted or unsubstituted alkyl group having 1 to 50 (preferably 1 to 20, more preferably 1 to 12, and particularly preferably 1 to 8) carbon atoms, a substituted or unsubstituted alkoxy group having 1 to 50 (preferably 1 to 20, more preferably 1 to 12, and particularly preferably 1 to 8) carbon atoms, a substituted or unsubstituted aralkyl group having 6 to 50 (preferably 6 to 20, more preferably 6 to 14) carbon atoms, a substituted or unsubstituted aryloxy group having 5 to 50 (preferably 5 to 20) ring atoms, a substituted or unsubstituted arylthio group having 5 to 50 (preferably 5 to 20) ring atoms, a substituted or unsubstituted alkoxycarbonyl group having 1 to 50 (preferably 1 to 20, more preferably 1 to 12, and particularly preferably 1 to 8) carbon atoms, a carboxyl group, a halogen atom, a cyano group, a nitro group and a hydroxy group, a, b and c are each an integer of 0 to 4.

n is an integer of 1 to 3, and when n is two or more, groups in the [ ] may be the same or different.

Here, when the above-mentioned groups shown by $Ar^{001}$ etc. have a substituent, the same groups as those shown by $R_a$ to $R_d$ in the formula (1) can be given as the substituent. They may be a substituted or unsubstituted amino group. In the context, when the groups shown in each formula stated later have a substituent, the same can be applied to the substituent. Asymmetrical monoanthracene derivatives represented by the following formula (ii):

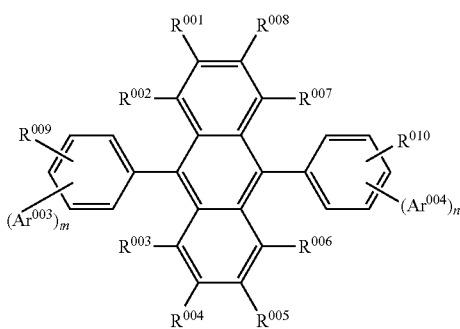

(ii)

wherein $Ar^{003}$ and $Ar^{004}$ are independently are a substituted or unsubstituted aromatic ring group having 6 to 50 (preferably 6 to 20, more preferably 6 to 14) ring carbon atoms, m and n are each an integer of 1 to 4, provided that in the case where m=n=1 and $Ar^{003}$ and $Ar^{004}$ are symmetrically bonded to the benzene rings, $Ar^{003}$ and $Ar^{004}$ are not the same, and in the case where m or n is an integer of 2 to 4, m is different from n, $R^{001}$ to $R^{010}$ are independently are a hydrogen atom, a substituted or unsubstituted aromatic ring group having 6 to 50 (preferably 6 to 20, more preferably 6 to 14) ring carbon atoms, a substituted or unsubstituted aromatic heterocyclic group having 5 to 50 (preferably 5 to 20) ring atoms, a substituted or unsubstituted alkyl group having 1 to 50 (preferably 1 to 20, more preferably 1 to 12 and particularly preferably 1 to 8) carbon atoms, a substituted or unsubstituted cycloalkyl group, a substituted or unsubstituted alkoxy group having 1 to 50 (preferably 1 to 20, more preferably 1 to 12, and particularly preferably 1 to 8) carbon atoms, a substituted or unsubstituted aralkyl group having 6 to 50 (preferably 6 to 20, more preferably 6 to 14) carbon atoms, a substituted or unsubstituted aryloxy group having 5 to 50 (preferably 5 to 20) ring atoms, a substituted or unsubstituted arylthio group having 5 to 50 (preferably 5 to 20) ring atoms, a substituted or unsubstituted alkoxycarbonyl group having 1 to 50 (preferably 1 to 20, more preferably 1 to 12, and particularly preferably 1 to 8) carbon atoms, a substituted or unsubstituted silyl group, a carboxyl group, a halogen atom, a cyano group, a nitro group or a hydroxyl group.

Asymmetrical pyrene derivatives shown by the following formula (iii):

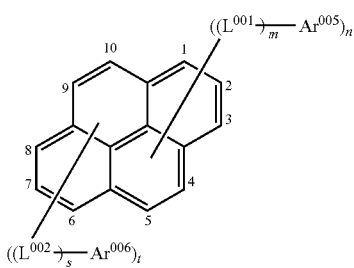

(iii)

wherein $Ar^{005}$ and $Ar^{006}$ are independently an aromatic group having 6 to 50 (preferably 6 to 20, more preferably 6 to 14) ring carbon atoms, $L^{001}$ and $L^{002}$ are independently a substituted or unsubstituted phenylene group, a substituted or unsubstituted naphthalenylene group, a substituted or unsubstituted fluolenylene group, or a substituted or unsubstituted dibenzosilolylene group, m is an integer of 0 to 2, n is an integer of 1 to 4, s is an integer of 0 to 2, and t is an integer of 0 to 4, $L^{001}$ or $Ar^{005}$ bonds at any one position of 1 to 5 of the pyrene, and $L^{002}$ or $Ar^{006}$ bonds at any one position of 6 to 10 of the pyrene; provided that when n+t is an even number, $Ar^{005}$, $Ar^{006}$, $L^{001}$ and $L^{002}$ satisfy the following (1) and (2):

(1) $Ar^{005} \neq Ar^{006}$ and/or $L^{001} \neq L^{002}$ where $\neq$ means these substituents are groups having different structures from each other, (2) when $Ar^{005} = Ar^{006}$ and $L^{001} = L^{002}$, (2-1) m≠s and/or n≠t, or (2-2) when m=s and n=t, (2-2-1) when $L^{001}$ and $L^{002}$ or pyrene are independently bonded to different bonding positions of $Ar^{005}$ and $Ar^{006}$, or (2-2-2) when $L^{001}$ and $L^{002}$ or pyrene are bonded to the same position of $Ar^{005}$ and $Ar^{006}$, the positions of the substitution of $L^{001}$ and $L^{002}$ or $Ar^{005}$ and $Ar^{006}$ at pyrene are neither the $1^{st}$ position and the $6^{th}$ position, nor the $2^{nd}$ position and the $7^{th}$ position.

Asymmetrical anthracene shown by the following formula (Iv):

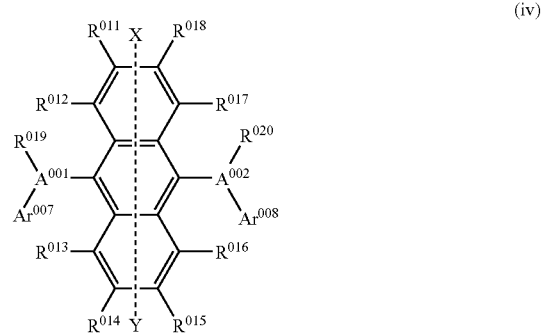

(iv)

wherein $A^{001}$ and $A^{002}$ are independently a substituted or unsubstituted fused aromatic ring group having 10 to 20 ring carbon atoms, $Ar^{007}$ and $Ar^{008}$ are independently a hydrogen atom or a substituted or unsubstituted aromatic ring group having 6 to 50 (preferably 6 to 20, more preferably 6 to 14) ring carbon atoms, $R^{011}$ to $R^{020}$ are independently are a hydrogen atom, a substituted or unsubstituted aromatic ring group having 6 to 50 (preferably 6 to 20, more preferably 6 to 14) ring carbon atoms, a substituted or unsubstituted aromatic heterocyclic group having 5 to 50 (preferably 5 to 20) ring atoms, a substituted or unsubstituted alkyl group having 1 to 50 (preferably 1 to 20, more preferably 1 to 12 and particularly preferably 1 to 8) carbon atoms, a substituted or unsubstituted cycloalkyl group, a substituted or unsubstituted alkoxy group having 1 to 50 (preferably 1 to 20, more preferably 1 to 12, and particularly preferably 1 to 8) carbon atoms, a substituted or unsubstituted aralkyl group having 6 to 50 (preferably 6 to 20, more preferably 6 to 14) carbon atoms, a substituted or unsubstituted aryloxy group having 5 to 50 (preferably 5 to 20) ring atoms, a substituted or unsubstituted arylthio group having 5 to 50 (preferably 5 to 20) ring atoms, a substituted or unsubstituted alkoxycarbonyl group having 1 to 50 (preferably 1 to 20, more preferably 1 to 12, and particularly preferably 1 to 8) carbon atoms, a substituted or unsubstituted silyl group, a carboxyl group, a halogen atom, a cyano group, a nitro group or a hydroxyl group, and there may be a plurality of $Ar^{007}$, $Ar^{008}$, $R^{019}$ and $R_{020}$, respectively, and adjacent groups thereof may form a saturated or unsaturated ring structure, provided that groups do not symmetrically bond to 9 and 10 positions of the central anthracene with respect to X-Y axis.
Anthracene derivative represented by the following formula (v):

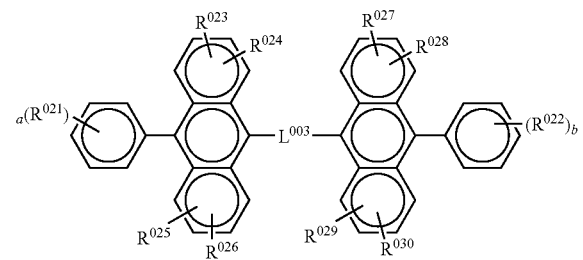

wherein $R^{021}$ to $R^{030}$ are independently a hydrogen atom, an alkyl group, a cycloalkyl group, a substituted or unsubstituted aryl group, an alkoxy group, an aryloxy group, an alkylamino group, an alkenyl group, an arylamino group or a substituted or unsubstituted heterocyclic group, a and b are independently an integer of 1 to 5, and when they are two or more, $R^{021}$s or $R^{022}$s may be the same or different, $R^{021}$s or $R^{022}$s may be bonded to form a ring, $R^{023}$ and $R^{024}$, $R^{025}$ and $R^{026}$, $R^{027}$ and $R^{028}$, and $R^{029}$ and $R^{030}$ may be bonded to each other to form a ring, and $L^{003}$ is a single bond, —O—, —S—, —N(R)— (R is an alkyl group or a substituted or unsubstituted aryl group), an alkylene group or an arylene group.
Anthracene derivative shown by the following formula (vi):

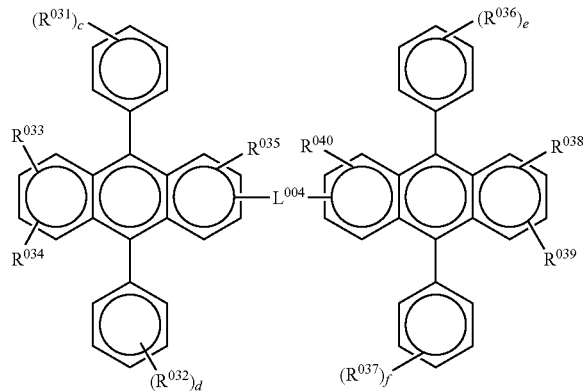

wherein $R^{031}$ to $R^{040}$ are independently a hydrogen atom, an alkyl group, a cycloalkyl group, an aryl group, an alkoxy group, an aryloxy group, an alkylamino group, an arylamino group or a substituted or unsubstituted heterocyclic group, c, d, e and f are independently an integer of 1 to 5, and when they are two or more, $R^{031}$s, $R^{032}$s, $R^{038}$s or $R^{037}$s may be the same or different, $R^{031}$s, $R^{032}$s, $R^{038}$s or $R^{037}$s may be bonded to form a ring, and $R^{033}$ and $R^{034}$, and $R^{038}$ and $R^{039}$ may be bonded to each other to form a ring, and $L^{004}$ is a single bond, —O—, —S—, —N(R)— (R is an alkyl group or a substituted or unsubstituted aryl group), an alkylene group or an arylene group.
Spirofluorene derivative represented by the following formula (vii):

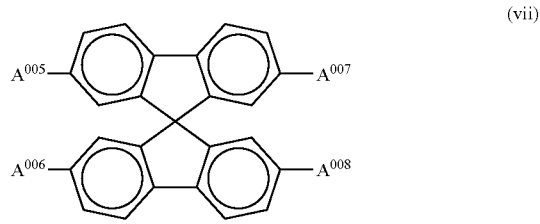

wherein $A^{005}$ to $A^{008}$ are independently a substituted or unsubstituted biphenyl or a substituted or unsubstituted naphthyl group.

Fused ring-containing compounds shown by the following formula (viii):

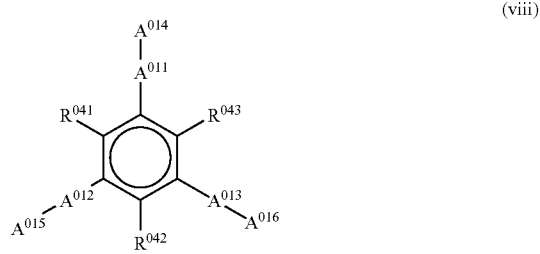

wherein $A^{011}$ to $A^{013}$ are independently a substituted or unsubstituted arylene group having 6 to 50 (preferably 6 to 20, more preferably 6 to 14) ring carbon atoms, $A^{014}$ to $A^{016}$ are independently a hydrogen atom or a substituted or unsubstituted aryl group having 6 to 50 (preferably 6 to 20, more preferably 6 to 14) ring carbon atoms, and $R^{041}$ to $R^{043}$ are independently a hydrogen atom, alkyl group having 1 to 6 carbon atoms, cycloalkyl group having 3 to 6 carbon atoms, alkoxy group having 1 to 6 carbon atoms, aryloxy group having 5 to 18 carbon atoms, aralkyloxy group having 7 to 18 carbon atoms, arylamino group having 5 to 16 carbon atoms, nitro group, cyano group, ester group having 1 to 6 carbon atoms, or a halogen atom, provided that at least one of $A^{011}$ to $A^{016}$ is a group having a fused aromatic ring with three or more rings.
Fluorene compounds shown by the following formula (ix):

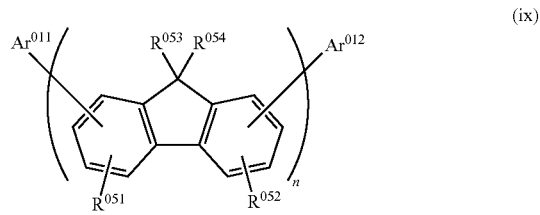

wherein $R^{051}$ and $R^{052}$ are a hydrogen atom, a substituted or unsubstituted alkyl group, a substituted or unsubstituted aralkyl group, a substituted or unsubstituted aryl group, a substituted or unsubstituted heterocyclic group, substituted amino group, cyano group, or a halogen atom, $R^{051}$s or $R^{052}$s bonded to different fluorene groups may be the same or different, and $R^{051}$ and $R^{052}$ bonded to a single fluorene group may be the same or different, $R^{053}$ and $R^{054}$ are independently a hydrogen atom, a substituted or unsubstituted alkyl group, a substituted or unsubstituted aralkyl group, a substituted or unsubstituted aryl group or a substituted or unsubstituted heterocyclic group, $R^{053}$s or $R^{054}$s bonded to different fluorene groups may be the same or different, and $R^{053}$ and $R^{054}$ bonded to a single fluorene group may be the same or different, and $Ar^{011}$ and $Ar^{012}$ are a substituted or unsubstituted fused polycyclic aromatic group with a total number of benzene rings of three or more or a fused polycyclic heterocyclic group which is bonded to the fluorene group through substituted or unsubstituted carbon and has a total number of benzene rings and heterocyclic rings of three or more, provided that $Ar^{011}$ and $Ar^{012}$ may be the same or different. n represents an integer of 1 to 10.

In the organic EL device of the invention, it is preferred that the emitting layer contain the compound of the invention as a host and contain at least one of a phosphorescent dopant and a fluorescent dopant. An emitting layer containing these dopants may be stacked on an emitting layer containing the compound of the invention.

A phosphorescent dopant is a compound that can emit light from triplet excitons. The dopant is not limited so long as it can emit light from triplet excitons, but it is preferably a metal complex containing at least one metal selected from the group of Ir, Ru, Pd, Pt, Os and Re. A porphyrin metal complex or an ortho-metalated metal complex is preferable. The phosphorescent compounds can be used individually or as a combination of two or more kinds.

As a porphyrin metal complex, a porphyrin platinum complex is preferable.

There are various ligands forming an ortho-metalated metal complex. Preferable ligands include compounds having a phenylpyridine skeleton, a bipyridyl skeleton or a phenanthroline skeleton, 2-phenylpyridine, 7,8-benzoquinoline, 2-(2-thienyl)pyridine, 2-(1-naphthyl)pyridine and 2-phenylquinoline derivatives. These ligands may have a substituent, if necessary. Ligands to which fluorides, e.g. a trifluoromethyl group, being introduced as a substituent are particularly preferable as a blue dopant. As an auxiliary ligand, preferred are ligands other than the above-mentioned ligands, such as acetylacetonate and picric acid may be contained.

Specific Examples of such a metal complex include tris(2-phenylpyridine)iridium, tris(2-phenylpyridine)ruthenium, tris(2-phenylpyridine)palladium, bis(2-phenylpyridine)platinum, tris(2-phenylpyridine)osmium, tris(2-phenylpyridine)rhenium, platinum octaethylporphyrin, platinum octaphenylporphyrin, palladium octaethylporphyrin, palladium octaphenylporphyrin and the like. However, the metal complex is not limited to these. An appropriate complex can be selected depending on required emitting colors and device performance, and host compounds used.

The content of a phosphorescent dopant in an emitting layer is not limited and can be properly selected according to purposes; for example, it is 0.1 to 70 mass %, preferably 1 to 30 mass %. When the content of a phosphorescent compound is less than 0.1 mass %, emission may be weak and the advantages thereof may not be sufficiently obtained. When the content exceeds 70 mass %, the phenomenon called concentration quenching may significantly proceed, thereby degrading the device performance.

As for the fluorescent dopant, it is preferable to select a compound from amine-based compounds, aromatic compounds, chelate complexes such as tris(8-quinolilate)aluminum complexes, coumarin derivatives, tetraphenylbutadiene derivatives, bisstyrylarylene derivatives, oxadiazole derivatives or the like, taking into consideration required emission colors. Of these, styrylamine compounds, styryldiamine compounds, arylamine compounds and aryldiamine compounds are further preferable. Fused polycyclic aromatic compounds which are not an amine compound are also preferable. These fluorescent dopants may be used singly or in combination of two or more.

The content of a fluorescent dopant in the emitting layer is not particularly limited and can be appropriately selected according to purposes; for example, it is 0.01 to 100 mass %, preferably 0.1 to 30 mass %.

As the styrylamine compound and the styryldiamine compound, those shown by the following formula (A) are preferable.

(A)

wherein $Ar^{101}$ is a group with a valence of p corresponding to a phenyl group, a naphthyl group, a biphenyl group, a terphenyl group, a stilbenzyl group or a distyrylaryl group, $Ar^{102}$ and $Ar^{103}$ are independently an aromatic hydrocarbon group having 6 to 20 (preferably 6 to 14) carbon atoms, $Ar^{101}$, $Ar^{102}$ and $Ar^{103}$ may be substituted, one of $Ar^{101}$ to $Ar^{103}$ is substituted by a styryl group, further preferably, at least one of $Ar^{102}$ and $Ar^{103}$ is substituted by a styryl group, and p is an integer of 1 to 4, preferably an integer of 1 to 2.

Here, as the aromatic hydrocarbon group having 6 to 20 (preferably 6 to 14) carbon atoms, a phenyl group, a naphthyl group, an anthranyl group, a phenanthryl group, a terphenyl group or the like can be given.

As the arylamine compound and the aryldiamine compound, those shown by the following formula (B) are preferable.

(B)

wherein $A^{111}$ is a substituted or unsubstituted aromatic group with a valence of q having 5 to 40 (preferably 6 to 20, more preferably 6 to 14) ring carbon atoms, $Ar^{112}$ and $Ar^{113}$ are independently a substituted or unsubstituted aryl group having 5 to 40 (preferably 6 to 20, more preferably 6 to 14) ring carbon atoms, and q is an integer of 1 to 4, preferably an integer of 1 to 2.

Examples of the aryl group having 5 to 40 ring carbon atoms include a phenyl group, a naphthyl group, an anthranyl group, a phenanthryl group, a pyrenyl group, a coronyl group, a biphenyl group, a terphenyl group, a pyrrolyl group, a furanyl group, a thiophenyl group, a benzothiophenyl group, an oxadiazolyl group, a diphenylanthranyl group, an indolyl group, a carbazolyl group, a pyridyl group, a benzoquinolyl group, a fluoranthenyl group, an acenaphthofluoranthenyl group, a stilbene group, a perylenyl group, a chrysenyl group, a picenyl group, a triphenylenyl group, a rubicenyl group, a benzanthracenyl group, a phenylanthranyl group and a bisanthracenyl group. Preferred are a naphthyl group, an anthranyl group, chrysenyl group and a pyrenyl group.

As the $Ar^{111}$, the above-mentioned q-valent group is preferable. When $Ar^{111}$ is a divalent group, groups shown by the following formulas (C) and (D) are preferable. A group shown by the formula (D) is more preferable.

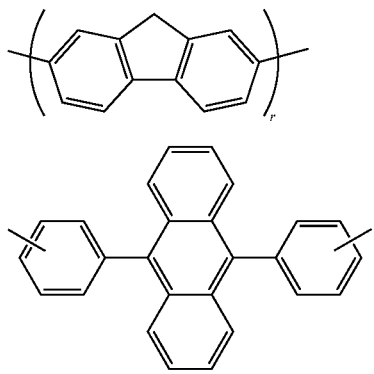

(in the formula (C), r is an integer of 1 to 3)

Preferred substituents for the above-mentioned aryl group include an alkyl group having 1 to 6 carbon atoms (ethyl, methyl, i-propyl, n-propyl, s-butyl, t-butyl, pentyl, hexyl, cyclopentyl, cyclohexyl, or the like); an alkoxy group having 1 to 6 carbon atoms (ethoxy, methoxy, i-propoxy, n-propoxy, s-buthoxy, t-buthoxy, penthoxy, hexyloxy, cyclopentoxy, cyclohexyloxy, or the like); an aryl group having 5 to 40 (preferably 6 to 20, more preferably 6 to 14) ring carbon atoms; an amino group substituted with an aryl group having 5 to 40 ring carbon atoms; an ester group with an aryl group having 5 to 40 ring carbon atoms; an ester group with an alkyl group having 1 to 6 carbon atoms; a cyano group; a nitro group; and a halogen atom.

The emitting layer may contain hole-transporting materials, electron-transporting materials and polymer binders, if necessary.

The thickness of an emitting layer is preferably from 5 to 50 nm, more preferably from 7 to 50 nm and most preferably from 10 to 50 nm. When it is less than 5 nm, the formation of an emitting layer and the adjustment of chromaticity may become difficult. When it exceeds 50 nm, the driving voltage may increase.

The hole-transporting layer and the hole-injecting layer are layers which help the injection of holes into the emitting layer so as to transport holes to an emitting region, and have a large hole mobility and normally have such a small ionization energy as 5.5 eV or less. As the material for the hole-injecting layer and the hole-transporting layer, a material which transports holes to the emitting layer at a lower electrical field is preferable, and the hole mobility thereof is preferably $10^{-4}$ $cm^2/V \cdot second$ or more when an electric field of, e.g., $10^4$ to $10^6$ V/cm is applied.

There are no particular restrictions on the material for the hole-injecting layer and the hole-transporting layer. The material can be arbitrarily selected from materials which have been widely used as a hole-transporting material of photoconductive materials and known materials used in a hole-injecting layer and a hole-transporting layer of organic EL devices.

In the hole-injecting layer and the hole-transporting layer, an aromatic amine derivative shown by the following formula can be used, for example.

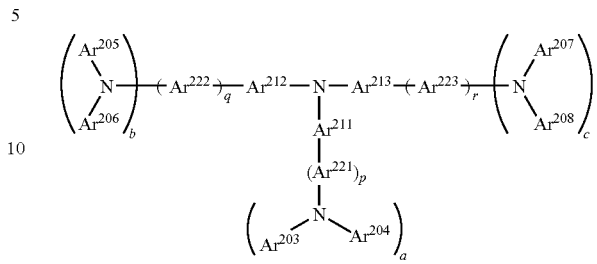

wherein $Ar^{211}$ to $Ar^{213}$, $Ar^{221}$ to $Ar^{223}$ and $Ar^{203}$ to $Ar^{208}$ are independently a substituted or unsubstituted aromatic hydrocarbon group having 6 to 50 (preferably 6 to 20, more preferably 6 to 14) ring carbon atoms or a substituted or unsubstituted aromatic heterocyclic group having 5 to 50 (preferably 5 to 20) ring atoms, a to c and p to r are independently an integer of 0 to 3, and $Ar^{203}$ and $Ar^{204}$, $Ar^{205}$ and $Ar^{206}$, or $Ar^{207}$ and $Ar^{208}$ may be bonded to each other to form a saturated or unsaturated ring.

Examples of the substituted or unsubstituted aromatic hydrocarbon groups having 6 to 50 ring carbon atoms include a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, and 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, and 4"-t-butyl-p-terphenyl-4-yl group.

Examples of the substituted or unsubstituted aromatic heterocyclic group having 5 to 50 ring atoms include a 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiadinyl group, 2-phenothiadinyl group, 3-phenothiadinyl group, 4-phenothiadinyl group, 10-phenothiadinyl group, 1-phenoxadinyl group, 2-phenoxadinyl group, 3-phenoxadinyl group, 4-phenoxadinyl group, 10-phenoxadinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

Further, the compound shown by the following formula can be used in the hole-injecting layer and the hole-transporting layer.

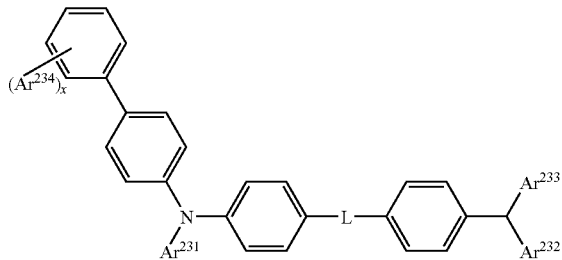

wherein $Ar^{231}$ to $Ar^{234}$ are independently a substituted or unsubstituted aromatic hydrocarbon group having 6 to 50 (preferably 6 to 20, more preferably 6 to 14) ring carbon atoms, or a substituted or unsubstituted aromatic heterocyclic group having 5 to 50 (preferably 5 to 20) ring atoms, L is a linking group, which is a single bond, a substituted or unsubstituted aromatic hydrocarbon group having 6 to 50 (preferably 6 to 20, more preferably 6 to 14) ring carbon atoms or a substituted or unsubstituted aromatic heterocyclic group having 5 to 50 (preferably 5 to 20) ring atoms, x is an integer of 0 to 5, and $Ar^{232}$ and $Ar^{233}$ may be bonded to each other to form a saturated or unsaturated ring.

As specific examples of the substituted or unsubstituted aromatic hydrocarbon group having 6 to 50 ring carbon atoms and substituted or unsubstituted aromatic heterocyclic group having 5 to 50 ring atoms, the same as those exemplified above for the aromatic amine derivative can be given.

As specific examples of the material for the hole-injecting layer and the hole-transporting layer, a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalkone derivative, an oxazole derivative, a styrylanthracene derivative, a fluorenone derivative, a hydrazone derivative, a stilbene derivative, a silazane derivative, an aniline-based copolymer, and conductive high-molecular oligomers (in particular, a thiophene oligomer) can be given.

As the material for the hole-injecting layer and the hole-transporting layer, although the above-mentioned materials can be used, it is preferable to use a porphyrin compound, an aromatic tertiary amine compound and a styrylamine compound. It is particularly preferable to use an aromatic tertiary amine compound.

It is preferable to use a compound having two fused aromatic rings in the molecule thereof, for example, 4,4'-bis(N-(1-naphthyl)-N-phenylamino)biphenyl (abbreviated by NPD, hereinafter), and 4,4',4"-tris(N-(3-methylphenyl)-N-phenylamino)triphenylamine (abbreviated by MTDATA, hereinafter) wherein three triphenylamine units are linked in a star-burst form.

In addition to the above, a nitrogen-containing heterocyclic derivative shown by the following formula can also be used.

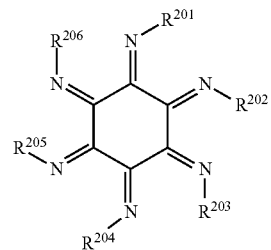

wherein $R^{201}$ to $R^{206}$ are independently a substituted or unsubstituted alkyl group, a substituted or unsubstituted aryl group, a substituted or unsubstituted aralkyl group, a substituted or unsubstituted heterocyclic group, and $R^{201}$ and $R^{202}$, $R^{203}$ and $R^{204}$, $R^{205}$ and $R^{206}$, $R^{201}$ and $R^{206}$, $R^{202}$ and $R^{203}$, or $R^{204}$ and $R^{205}$ may form a fused ring.

Further, the following compound can also be used.

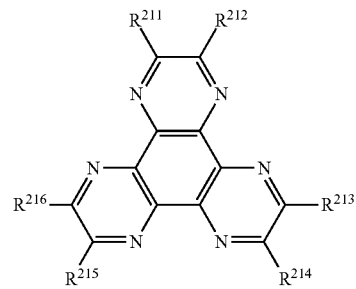

wherein $R^{211}$ to $R^{216}$ are substituents; preferably they are independently an electron-attracting group such as a cyano group, a nitro group, a sulfonyl group, a carbonyl group, a trifluoromethyl group and a halogen.

Further, an inorganic compound such as p-type Si and p-type SiC can also be used as a material for the hole-injecting layer and the hole-transporting layer.

The hole-injecting layer and the hole-transporting layer can be formed from the above-mentioned compounds by a known method such as vapor vacuum deposition, spin coating, casting or LB technique. The film thickness of the hole-injecting layer and the hole-transporting layer is not particularly limited, and is usually from 5 nm to 5 µm. The hole-injecting layer and the hole-transporting layer may be a single layer made of one or two or more of the above-mentioned materials, or may be of a structure in which hole-injecting layers and hole-transporting layers made of different compounds are stacked.

The organic semiconductor layer is a layer for helping the injection of holes or electrons into the emitting layer, and is preferably a layer having an electric conductivity of $10^{-10}$ S/cm or more. As the material of such an organic semiconductor layer, electroconductive oligomers such as thiophene-containing oligomers or arylamine-containing oligomers and electroconductive dendrimers such as arylamine-containing dendrimers may be used.

The electron-injecting layer and the electron-transporting layer are layers which assist injection of electrons into the emitting layer and transport electrons to the emitting region, and exhibit a high electron mobility. The adhesion-improving layer is a kind of the electron-injecting layer which is made of a material exhibiting particularly good adhesion to the cathode.

The thickness of the electron-transporting layer is arbitrarily selected in the range of 5 nm to 5 µm. When the electron-transporting layer has a thick thickness, it is preferable that the electron mobility be $10^{-5}$ cm$^2$/Vs or more at an applied electric field of $10^4$ to $10^6$ V/cm in order to prevent an increase in voltage.

The material used in the electron-injecting layer and the electron-transporting layer is preferably a metal complex of 8-hydroxyquinoline or a derivative thereof, or an oxadiazole derivative. Specific examples of the metal complex of 8-hydroxyquinoline or derivative thereof include metal chelate oxynoid compounds containing a chelate of oxine (generally, 8-quinolinol or 8-hydroxyquinoline), e.g. tris(8-quinolinolato)aluminum.

As examples of the oxadiazole derivative, an electron-transporting compound shown by the following formula can be given.

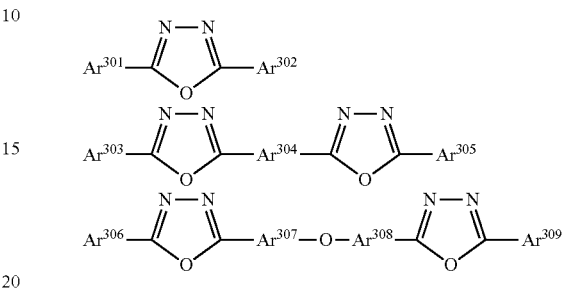

wherein Ar$^{301}$, Ar$^{302}$, Ar$^{303}$, Ar$^{305}$, Ar$^{306}$ and Ar$^{309}$ are independently a substituted or unsubstituted aryl group, and Ar$^{304}$, Ar$^{307}$ and Ar$^{308}$ are independently a substituted or unsubstituted arylene group.

As examples of the aryl group, a phenyl group, a biphenyl group, an anthranyl group, a perylenyl group, and a pyrenyl group can be given. As examples of the arylene group, a phenylene group, a naphthylene group, a biphenylene group, an anthranylene group, a perylenylene group, a pyrenylene group, and the like can be given. As the substituent, an alkyl group having 1 to 10 carbon atoms, an alkoxy group having 1 to 10 carbon atoms, a cyano group, and the like can be given. The electron-transporting compound is preferably one from which a thin film can be formed.

The following compounds can be given as specific examples of the electron-transporting compound.

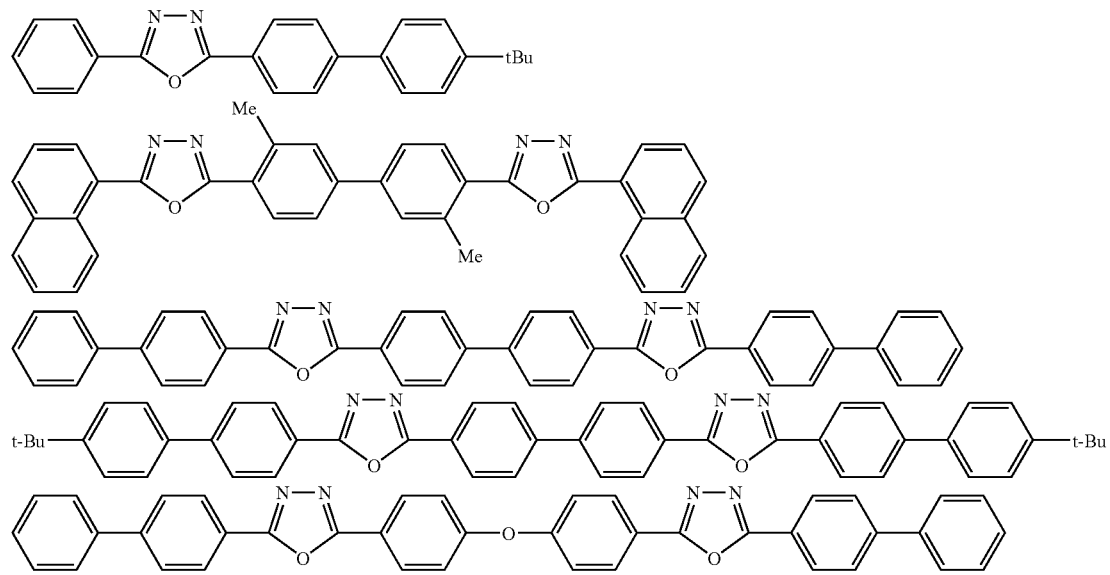

(Me is Methyl and tBu is T-Butyl.)

Furthermore, as materials used for the electron-injecting layer and electron-transporting layer, the compounds represented by the following formulas (E) to (J) may be used.

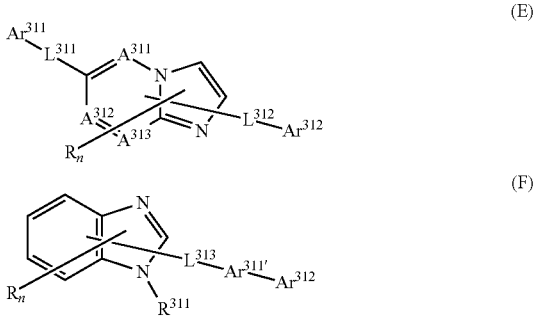

(E)

(F)

Nitrogen-containing heterocyclic derivatives shown by the formulas (E) and (F): wherein $Ar^{311}$ to $Ar^{313}$ are independently a nitrogen atom or a carbon atom, $Ar^{311}$ is a substituted or unsubstituted aryl group having 6 to 60 (preferably 6 to 20, more preferably 6 to 14) ring carbon atoms or a substituted or unsubstituted heteroaryl group having 3 to 60 (preferably 3 to 20, more preferably 3 to 14) ring atoms, $Ar^{311'}$ is an arylene group having 6 to 60 (preferably 6 to 20, more preferably 6 to 14) ring atoms or a substituted or unsubstituted heteroarylene group having 3 to 60 (preferably 3 to 20, more preferably 3 to 14) ring carbon atoms, and $Ar^{312}$ is a hydrogen atom, a substituted or unsubstituted aryl group having 6 to 60 (preferably 6 to 20, more preferably 6 to 14) ring carbon atoms, a substituted or unsubstituted heteroaryl group having 3 to 60 (preferably 3 to 20, more preferably 3 to 14) ring atoms, a substituted or unsubstituted alkyl group having 1 to 20 (preferably 1 to 12, more preferably 1 to 8) carbon atoms, or a substituted or unsubstituted alkoxy group having 1 to 20 (preferably 1 to 12, more preferably 1 to 8) carbon atoms, provided that one of $Ar^{311}$ and $Ar^{312}$ is a substituted or unsubstituted fused ring group having 10 to 60 (preferably 10 to 30, more preferably 10 to 20) ring carbon atoms or a substituted or unsubstituted monohetero fused ring group having 3 to 60 (preferably 3 to 20, more preferably 3 to 14) ring atoms, $L^{311}$, $L^{312}$ and $L^{313}$ are independently a single bond, a substituted or unsubstituted arylene group having 6 to 60 ring carbon atoms, a substituted or unsubstituted heteroarylene group having 3 to 60 ring atoms, or a substituted or unsubstituted fluorenylene group, R and $R^{311}$ are independently a hydrogen atom, a substituted or unsubstituted aryl group having 6 to 60 ring carbon atoms, a substituted or unsubstituted heteroaryl group having 3 to 60 ring atoms, a substituted or unsubstituted alkyl group having 1 to 20 (preferably 1 to 12, more preferably 1 to 8) carbon atoms, or a substituted or unsubstituted alkoxy group having 1 to 20 (preferably 1 to 12, more preferably 1 to 8) carbon atoms, n is an integer of 0 to 5, and when n is two or more, plural Rs may be the same or different, and adjacent Rs may be bonded to each other to form a carbocyclic aliphatic ring or a carbocyclic aromatic ring.

$$HAr-L^{314}-Ar^{321}-Ar^{322}$$ (G)

Nitrogen-containing heterocyclic derivatives shown by the formula (G):

wherein HAr is a nitrogen-containing heterocyclic ring having 3 to 40 (preferably 3 to 30, more preferably 3 to 24) carbon atoms, which may have a substituent, $L^{314}$ is a single bond, an arylene group having 6 to 60 (preferably 6 to 20, more preferably 6 to 14) carbon atoms, which may have a substituent, an heteroarylene group having 3 to 60 (preferably 3 to 20, more preferably 3 to 14) carbon atoms, which may have a substituent, or a fluorenylene group which may have a substituent, $Ar^{321}$ is a divalent aromatic hydrocarbon group having 6 to 60 (preferably 6 to 20, more preferably 6 to 14) carbon atoms, which may have a substituent, and $Ar^{322}$ is a an aryl group having 6 to 60 (preferably 6 to 20, more preferably 6 to 14) carbon atoms, which may have a substituent or a heteroaryl group having 3 to 60 (preferably 3 to 20, more preferably 3 to 14) carbon atoms, which may have a substituent.

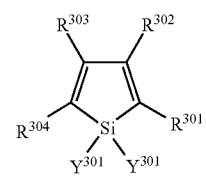

(H)

Silacyclopentadiene derivatives shown by the formula (H) wherein $X^{301}$ and $Y^{301}$ are independently a saturated or unsaturated hydrocarbon group having 1 to 6 carbon atoms, an alkoxy group, an alkenyloxy group, an alkynyloxy group, a hydroxyl group, a substituted or unsubstituted aryl group, or a substituted or unsubstituted hetero ring, or X and Y are bonded to form a saturated or unsaturated ring, and $R^{301}$ to $R^{304}$ are independently hydrogen, halogen, an alkyl group, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group. These groups may be substituted and adjacent groups may form a substituted or unsubstituted fused ring.

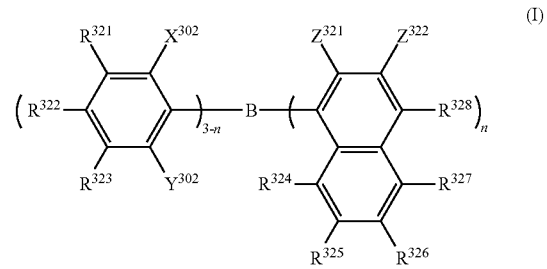

(I)

Borane derivatives shown by the formula (1) wherein $R^{321}$ to $R^{328}$ and $Z^{322}$ are independently a hydrogen atom, a saturated or unsaturated hydrocarbon group, an aromatic hydrocarbon group, a heterocyclic group, a substituted amino group, a substituted boryl group, an alkoxy group, or an aryloxy group, $X^{302}$, $Y^{302}$, and $Z^{321}$ are independently a saturated or unsaturated hydrocarbon group, an aromatic hydrocarbon group, a heterocyclic group, a substituted amino group, an alkoxy group, or an aryloxy group, $Z^{321}$ and $Z^{322}$ may be bonded to form a fused ring, and n is an integer of 1 to 3, provided that when n or (3-n) is two or more, $R^{321}$ to $R^{328}$, $X^{302}$, $Y^{302}$, $Z^{322}$ and $Z^{321}$ may be the same or different, provided that compounds where n is 1, $X^{302}$, $Y^{302}$, and $R^{322}$ are methyl groups, and $R^{328}$ is a hydrogen atom or a substituted boryl group, and compounds where n is 3 and $Z^{321}$ is a methyl group are excluded.

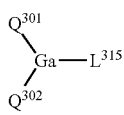
(J)

Gallium complexes shown by the formula (J) wherein $Q^{301}$ and $Q^{302}$ are independently ligands represented by the following formula (K) and $L^{315}$ is a halogen atom, a substituted or unsubstituted alkyl group, a substituted or unsubstituted cycloalkyl group, a substituted or unsubstituted aryl group, a substituted or unsubstituted heterocyclic group, —OR (R is a hydrogen atom, a substituted or unsubstituted alkyl group, a substituted or unsubstituted cycloalkyl group, a substituted or unsubstituted aryl group, or a substituted or unsubstituted heterocyclic group) or a ligand represented by —O—Ga—$Q^{303}(Q^{304})$ wherein $Q^{303}$ and $Q^{304}$ are the same as $Q^{301}$ and $Q^{302}$.

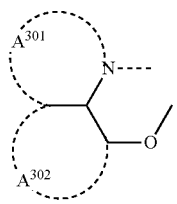
(K)

wherein rings $A^{301}$ and $A^{302}$ are independently a 6-membered aryl ring structure which may have a substituent and they are fused to each other.

The metal complexes have the strong nature of an n-type semiconductor and large ability of injecting electrons. Further, the energy generated at the time of forming a complex is small so that a metal is then strongly bonded to ligands in the complex formed and the fluorescent quantum efficiency becomes large as the emitting material.

Specific examples of the substituents for the rings $A^{301}$ and $A^{302}$ forming the ligand of the formula (K) include halogen atoms such as chlorine, bromine, iodine, and fluorine, substituted or unsubstituted alkyl groups such as a methyl group, ethyl group, propyl group, butyl group, sec-butyl group, tert-butyl group, pentyl group, hexyl group, heptyl group, octyl group, stearyl group, and trichloromethyl group, substituted or unsubstituted aryl groups such as a phenyl group, naphthyl group, biphenyl group, anthranyl group, phenanthryl group, fluorenyl group, pyrenyl group, 3-methylphenyl group, 3-methoxyphenyl group, 3-fluorophenyl group, 3-trichloromethylphenyl group, 3-trifluoromethylphenyl group, and 3-nitrophenyl group, substituted or unsubstituted alkoxy groups such as a methoxy group, n-butoxy group, tert-butoxy group, trichloromethoxy group, trifluoroethoxy group, pentafluoropropoxy group, 2,2,3,3-tetrafluoropropoxy group, 1,1,1,3,3,3-hexafluoro-2-propoxy group, and 6-(perfluoroethyl)hexyloxy group, substituted or unsubstituted aryloxy groups such as a phenoxy group, p-nitrophenoxy group, p-tert-butylphenoxy group, 3-fluorophenoxy group, pentafluorophenoxy group, and 3-trifluoromethylphenoxy group, substituted or unsubstituted alkylthio groups such as a methylthio group, ethylthio group, tert-butylthio group, hexylthio group, octylthio group, and trifluoromethylthio group, substituted or unsubstituted arylthio groups such as a phenylthio group, p-nitrophenylthio group, p-tert-butylphenylthio group, 3-fluorophenylthio group, pentafluorophenylthio group, and 3-trifluoromethylphenylthio group, a cyano group, a nitro group, an amino group, mono- or di-substituted amino groups such as a methylamino group, dimethylamino group, ethylamino group, diethylamino group, dipropylamino group, dibutylamino group, and diphenylamino group, acylamino groups such as a bis(acetoxymethyl)amino group, bis(acetoxyethyl)amino group, bis(acetoxypropyl)amino group, and bis(acetoxybutyl)amino group, a hydroxyl group, a siloxy group, an acyl group, substituted or unsubstituted carbamoyl groups such as a carbamoyl group, methylcarbamoyl group, dimethylcarbamoyl group, ethylcarbamoyl group, diethylcarbamoyl group, propylcarbamoyl group, butylcarbamoyl group, and phenylcarbamoyl group, a carboxylic acid group, a sulfonic acid group, an imide group, cycloalkyl groups such as a cyclopentane group and cyclohexyl group, heterocyclic groups such as a pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morpholidinyl group, piperazinyl group, carbazolyl group, furanyl group, thiophenyl group, oxazolyl group, oxadiazolyl group, benzoxazolyl group, thiazolyl group, thiadiazolyl group, benzothiazolyl group, triazolyl group, imidazolyl group, and benzimidazolyl group. The above substituents may be bonded to form a further six-membered aryl ring or heterocyclic ring.

A preferred embodiment of the organic EL device is a device containing a reducing dopant in an electron-transferring region or in an interfacial region between a cathode and an organic layer. The reducing dopant is defined as a substance which can reduce an electron-transferring compound. Accordingly, various substances which have given reducing properties can be used. For example, at least one substance can be preferably used which is selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, alkali metal carbonates, alkaline earth metal carbonates, rare earth metal carbonates, alkali metal organic complexes, alkaline earth metal organic complexes, and rare earth metal organic complexes.

More specific examples of the preferred reducing dopants include at least one alkali metal selected from the group consisting of Na (work function: 2.36 eV), K (work function: 2.28 eV), Rb (work function: 2.16 eV) and Cs (work function: 1.95 eV), and at least one alkaline earth metal selected from the group consisting of Ca (work function: 2.9 eV), Sr (work function: 2.0 to 2.5 eV), and Ba (work function: 2.52 eV). Metals having a work function of 2.9 eV or less are particularly preferred. Among these, a more preferable reducing dopant is at least one alkali metal selected from the group consisting of K, Rb and Cs. Even more preferable is Rb or Cs. Most preferable is Cs. These alkali metals are particularly high in reducing ability. Thus, the addition of a relatively small amount thereof to an electron-injecting zone improves the luminance of the organic EL device and make, the lifetime thereof long. As a reducing agent having a work function of 2.9 eV or less, combinations of two or more alkali metals are preferable, particularly combinations including Cs, such as Cs and Na, Cs and K, Cs and Rb, or Cs, Na and K are preferable. The combination containing Cs makes it possible to exhibit the reducing ability efficiently. The luminance of the organic EL device can be improved and the lifetime thereof can be made long by the addition thereof to its electron-injecting zone.

An electron-injecting layer made of an insulator or a semiconductor may further be provided between a cathode and an organic layer. By forming the electron-injecting layer, a current leakage can be effectively prevented and electron-injecting properties can be improved. If the electron-injecting layer is an insulating thin film, more uniformed thin film can be formed whereby pixel defects such as a dark spot are decreased.

As the insulator, at least one metal compound selected from the group consisting of alkali metal calcogenides, alkaline earth metal calcogenides, halides of alkali metals and halides of alkaline earth metals can be preferably used. When the electron-injecting layer is formed of the alkali metal calcogenide or the like, the injection of electrons can be preferably further improved. Specifically preferable alkali metal calcogenides include $Li_2O$, $K_2O$, $Na_2S$, $Na_2Se$ and $Na_2O$ and preferable alkaline earth metal calcogenides include CaO, BaO, SrO, BeO, BaS and CaSe. Preferable halides of alkali metals include LiF, NaF, KF, CsF, LiCl, KCl and NaCl. Preferable halides of alkaline earth metals include fluorides such as $CaF_2$, $BaF_2$, $SrF_2$, $MgF_2$ and $BeF_2$ and the other halides corresponding to the fluorides.

Semiconductors forming an electron-injecting layer include one or combinations of two or more of oxides, nitrides, and oxidized nitrides containing at least one element of Ba, Ca, Sr, Yb, Al, Ga, In, Li, Na, Cd, Mg, Si, Ta, Sb and Zn. An inorganic compound forming an electron-injecting layer is preferably a microcrystalline or amorphous insulating thin film.

For the cathode, the following may be used: an electrode substance made of a metal, an alloy or an electroconductive compound, or a mixture thereof which has a small work function (for example, 4 eV or less). Specific examples of the electrode substance include sodium, sodium-potassium alloy, magnesium, lithium, cesium, magnesium/silver alloy, aluminum/aluminum oxide, $Al/Li_2O$, Al/LiO, Al/LiF, aluminum/lithium alloy, indium, and rare earth metals.

The cathode is formed from these electrode materials by vapor deposition, sputtering or the like.

In the case where emission from the emitting layer is out-coupled through the cathode, it is preferred to make the transmittance of the cathode to the emission larger than 10%. The sheet resistance of the cathode is preferably several hundreds $\Omega/\square$ or less, and the film thickness thereof is usually from 10 nm to 1 µm, preferably from 50 to 200 nm.

Generally, in the organic EL device, pixel defects based on leakage or a short circuit are easily generated since an electric field is applied to the super thin film. In order to prevent this, it is preferred to insert an insulating thin layer between the pair of electrodes.

Examples of the material used in the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture or laminate thereof may be used.

As for the method for fabricating the organic EL device, it can be fabricated by forming necessary layers sequentially from the anode using the materials and the method as mentioned above, and finally forming the cathode. The organic EL device can be fabricated in the order reverse to the above, i.e., the order from the cathode to the anode.

An example of the fabrication of the organic EL device will be described below which has a structure wherein the following are successively formed on a transparent substrate: anode/hole-injecting layer/emitting layer/electron-injecting layer/cathode.

At first, a thin film formed of an anode material is formed on a transparent substrate by vapor deposition or sputtering to form an anode.

Next, a hole-injecting layer is formed on this anode. As described above, the hole-injecting layer can be formed by vacuum deposition, spin coating, casting, LB technique, or some other method. Vacuum deposition is preferred since a homogenous film is easily obtained and pinholes are not easily generated. In the case where the hole-injecting layer is formed by vacuum deposition, conditions for the deposition vary depending upon a compound used (a material for the hole-injecting layer), a desired structure of the hole-injecting layer, and others. In general, the conditions are preferably selected from the following: deposition source temperature of 50 to 450° C., vacuum degree of $10^{-7}$ to $10^{-3}$ Torr, vapor deposition rate of 0.01 to 50 nm/second, and substrate temperature of −50 to 300° C.

Next, an emitting layer is formed on the hole-injecting layer. The emitting layer can also be formed by making a luminescent material into a thin film by vacuum vapor deposition, sputtering, spin coating, casting or some other method. Vacuum vapor deposition is preferred since a homogenous film is easily obtained and pinholes are not easily generated. In the case where the emitting layer is formed by vacuum vapor deposition, conditions for the deposition, which vary depending on a compound used, can be generally selected from conditions similar to those for the hole-injecting layer.

Next, an electron-injecting layer is formed on the emitting layer. Like the hole-injecting layer and the emitting layer, the layer is preferably formed by vacuum vapor deposition because a homogenous film is required. Conditions for the deposition can be selected from conditions similar to those for the hole-injecting layer and the emitting layer.

Lastly, a cathode is stacked thereon to obtain an organic EL device. The cathode can be formed by vapor deposition or sputtering. However, vapor vacuum deposition is preferred in order to protect underlying organic layers from being damaged when the cathode film is formed.

For the organic EL device fabrication described above, it is preferred that the formation from the anode to the cathode is continuously carried out, using only one vacuuming operation.

The method for forming each of the layers in the organic EL device is not particularly limited. An organic thin film layer containing the compound of the invention can be formed by a known method such as vacuum vapor deposition, molecular beam epitaxy (MBE), or an applying coating method using a solution in which the compound is dissolved in a solvent, such as dipping, spin coating, casting, bar coating, or roll coating.

EXAMPLES

The invention will be specifically explained with reference to Examples below.

Synthesis Example 1

Synthesis of 5-bromobenzo[c]phenanthrene 5-bromobenzo[c]phenanthrene was synthesized according to the following synthesis scheme.

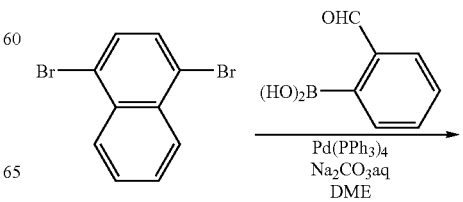

-continued

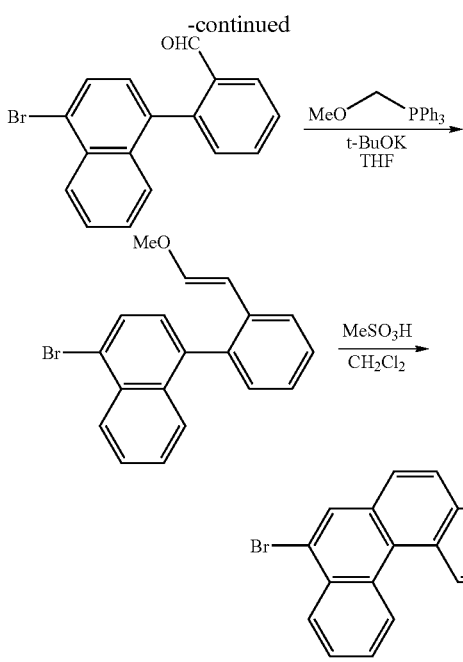

Under an argon atmosphere, 230 g of 1,4-dibromonaphthalene, 121 g of 2-formylphenylboronic acid and 18.5 g of tetraxis(triphenylphosphine)palladium(0) were placed in a flask. 2.4 L of dimethyl ether (DME) and 1.2 L of a 2M aqueous sodium carbonate solution were added to this flask, and the resultant was refluxed with stirring while heating for 8 hours. After cooling to room temperature, an aqueous phase was removed. An organic phase which had been separated was washed with water, and saturated brine, and then dried with magnesium sulfate. After the magnesium sulfate was filtered out, the organic phase was concentrated. The resulting residue was purified by means of silica gel column chromatography, whereby 170 g (yield: 67%) of 1-bromo-4-(2-formylphenyl) naphthalene was obtained.

Under an argon atmosphere, 170 g of the resulting 1-bromo-4-(2-formylphenyl)naphthalene, 207 g of methoxymethyl triphenylphosphonium chloride and 2.0 L of tetrahydrofuran (THF) were placed in a flask. During stirring at room temperature, 73.6 g of potassium t-butoxide was added to the flask. After further stirring at room temperature for 2 hours, 1.5 L of water was added. The reaction solution was extracted with diethyl ether. An aqueous phase was removed and an organic phase which had been separated was washed with water and saturated brine, and then dried with magnesium sulfate. After the magnesium sulfate was filtered out, the organic phase was concentrated. The resulting residue was purified by means of silica gel column chromatography, whereby 180 g (yield: 99%) of 1-bromo-4-[1-(2-methoxyvinyl)phenyl]naphthalene was obtained.

180 g of the 1-bromo-4-[1-(2-methoxyvinyl) phenyl]naphthalene obtained and 1.0 L of dichloromethane were placed in a flask. During stirring at room temperature, 25 mL of methanesulfonic acid were added to the flask. Stirring was conducted at room temperature for 8 hours. After the completion of the reaction, 1 L of a 10% aqueous solution of potassium carbonate was added. An aqueous phase was removed and an organic phase which had been separated was washed with water and saturated brine, and then dried with magnesium sulfate. After the magnesium sulfate was filtered out, the organic phase was concentrated. The resulting residue was purified by means of silica gel column chromatography, whereby 24.4 g (yield: 15%) of 5-bromobenzo[c]phenanthrene was obtained.

Example 1

Compound 1 was synthesized according to the following synthesis scheme.

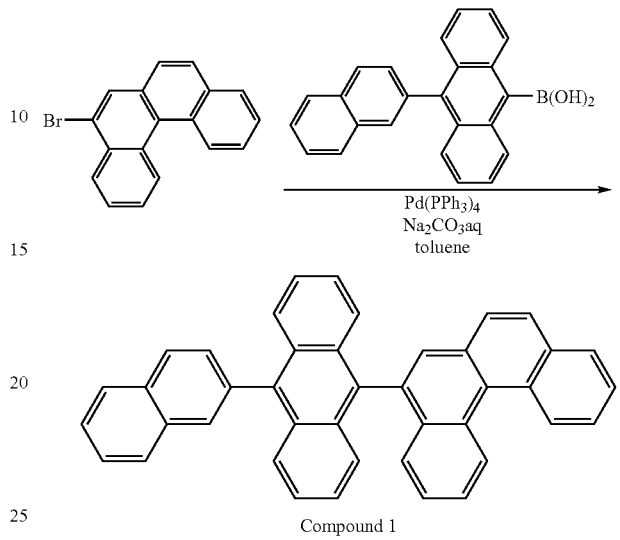

Compound 1

Under an argon atmosphere, 3.07 g of the 5-bromobenzo[c]phenanthrene which had been prepared in Synthesis Example 1, 4.18 g of 10-(2-naphthyl)anthracene-9-boronic acid which had been synthesized by a known method, 0.231 g of tetraxis(triphenylphosphine)palladium(0), 40 mL of toluene and 20 mL of a 2M aqueous solution of sodium carbonate were charged. The resultant was refluxed with stirring for 8 hours. After cooling to room temperature, the reaction solution was extracted with toluene. An aqueous phase was removed, and an organic phase which had been separated was washed with water and saturated brine sequentially, and then dried with magnesium sulfate. After the magnesium sulfate was filtered out, the organic phase was concentrated. The resulting residue was purified by a silica gel column chromatography, whereby 4.13 g of pale yellow crystals were obtained. As a result of mass spectrometry, the resulting crystals were confirmed to be the above-mentioned compound 1. The compound 1 had an m/e value of 530 with respect to a molecular weight of 530.20.

Example 2

Compound 2 was synthesized according to the following synthesis scheme.

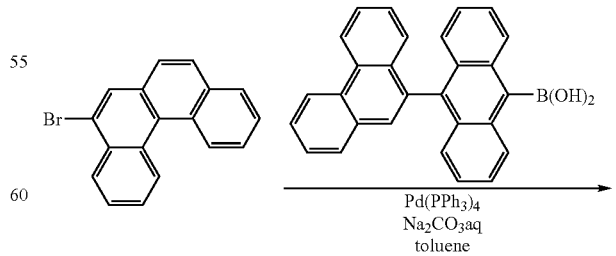

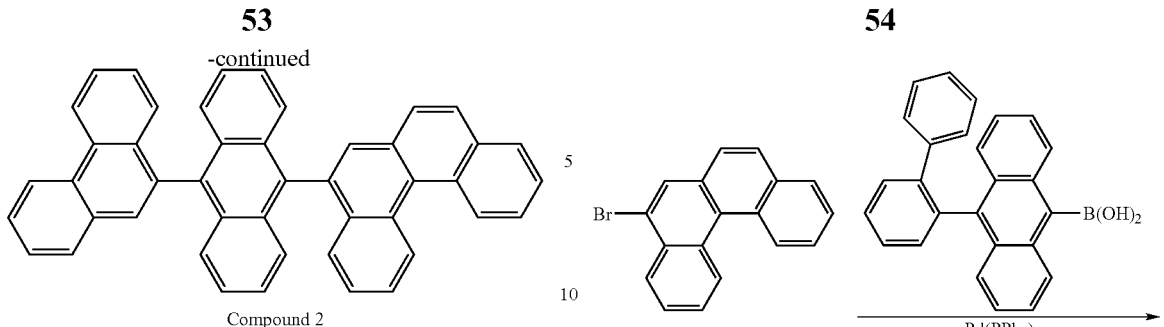

Compound 2

Crystals were synthesized and obtained in the same manner as in Example 1, except that 10-(9-phenanthryl)anthracene-9-boronic acid which had been synthesized by a known method was used instead of the 10-(2-naphthyl)anthracene-9-boronic acid. As a result of mass spectrometry, the resulting crystals were confirmed to be the compound 2. The compound 2 had an m/e value of 580 with respect to a molecular weight of 580.22.

Example 3

Compound 3 was synthesized according to the following synthesis scheme.

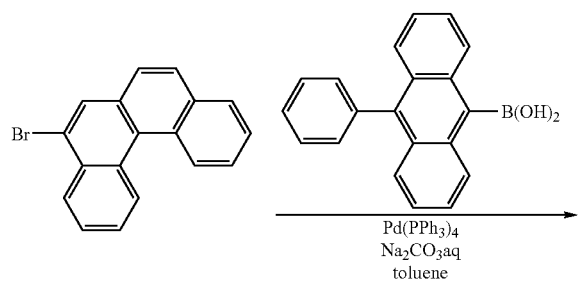

Compound 3

Crystals were synthesized and obtained in the same manner as in Example 1, except that 10-phenylanthracene-9-boronic acid which had been synthesized by a known method was used instead of the 10-(2-naphthyl)anthracene-9-boronic acid. As a result of mass spectrometry, the resulting crystals were confirmed to be the compound 3. The compound 3 had an m/e value of 480 with respect to a molecular weight of 480.19.

Example 4

Compound 4 was synthesized according to the following synthesis scheme.

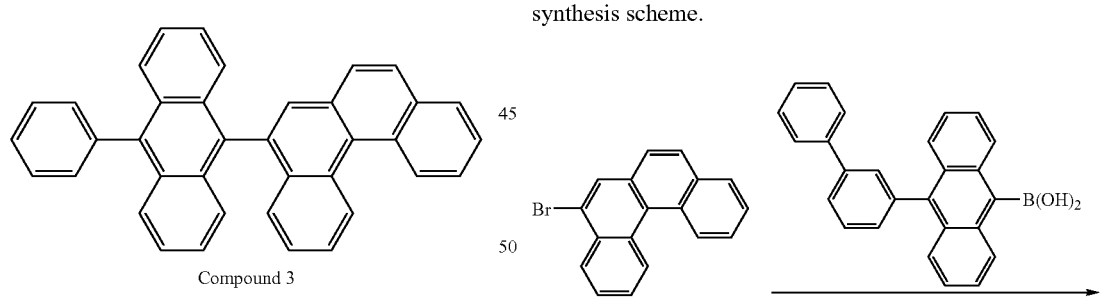

Compound 4

Crystals were synthesized and obtained in the same manner as in Example 1, except that 10-(2-biphenyl)anthracene-9-boronic acid which had been synthesized by a known method was used instead of the 10-(2-naphthyl)anthracene-9-boronic acid. As a result of mass spectrometry, the resulting crystals were confirmed to be the compound 4. The compound 4 had an m/e value of 556 with respect to a molecular weight of 556.22.

Example 5

Compound 5 was synthesized according to the following synthesis scheme.

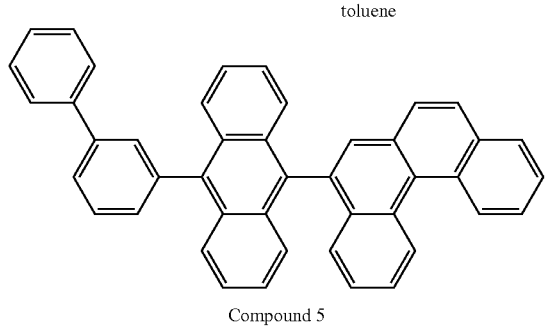

Compound 5

Crystals were synthesized and obtained in the same manner as in Example 1, except that 10-(3-biphenyl)anthracene-9-boronic acid which had been synthesized by a known method was used instead of the 10-(2-naphthyl)anthracene-9-boronic acid. As a result of mass spectrometry, the resulting crystals were confirmed to be the compound 5. The compound 5 had an m/e value of 556 with respect to a molecular weight of 556.22.

Example 6

Compound 6 was synthesized according to the following synthesis scheme.

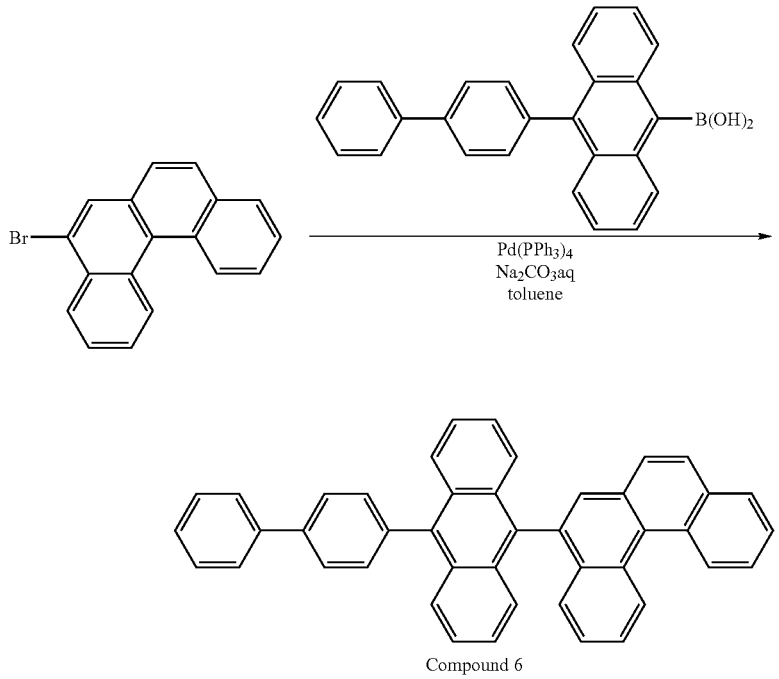

Compound 6

Crystals were synthesized and obtained in the same manner as in Example 1, except that 10-(4-biphenyl)anthracene-9-boronic acid which had been synthesized by a known method was used instead of the 10-(2-naphthyl)anthracene-9-boronic acid. As a result of mass spectrometry, the resulting crystals were confirmed to be the compound 6. The compound 6 had an m/e value of 556 with respect to a molecular weight of 556.22.

Example 7

Compound 7 was synthesized according to the following synthesis scheme.

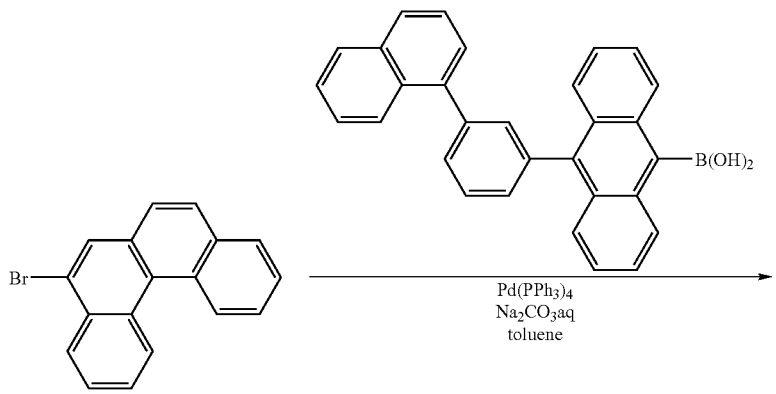

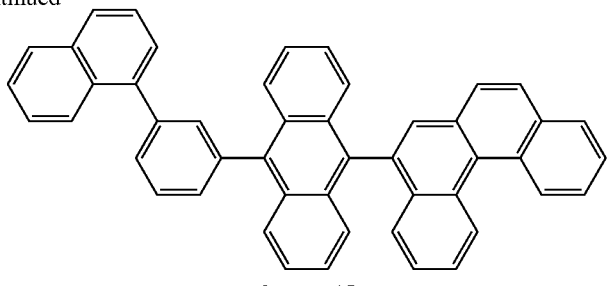

Compound 7

Crystals were synthesized and obtained in the same manner as in Example 1, except that 10-[3-(1-naphthyl)phenyl]anthracene-9-boronic acid which had been synthesized by a known method was used instead of the 10-(2-naphthyl)anthracene-9-boronic acid. As a result of mass spectrometry, the resulting crystals were confirmed to be the compound 7. The compound 7 had an m/e value of 606 with respect to a molecular weight of 606.23.

Example 8

Compound 8 was synthesized according to the following synthesis scheme.

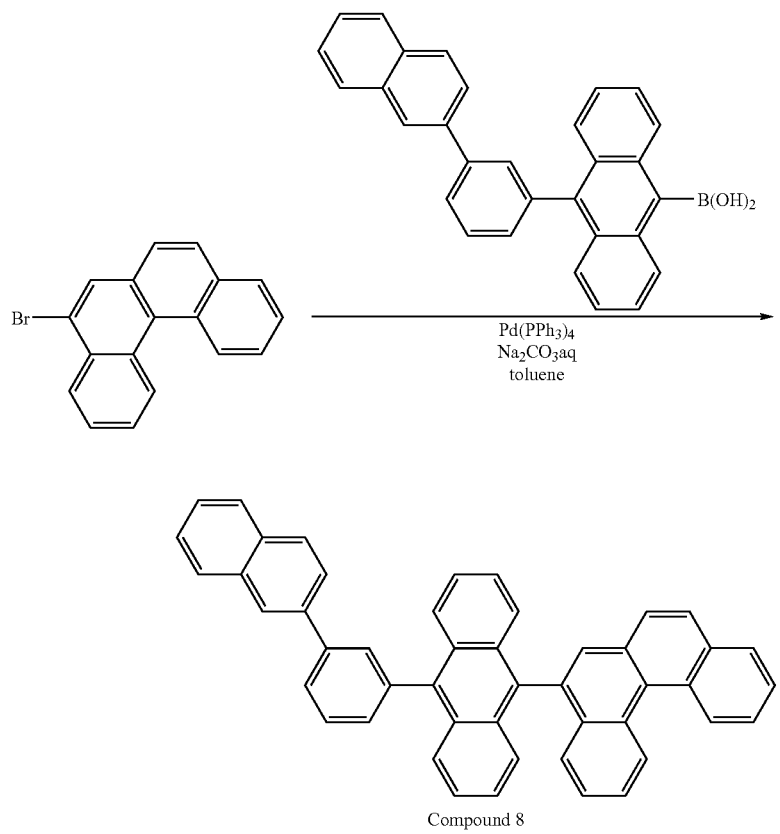

Compound 8

Crystals were synthesized and obtained in the same manner as in Example 1, except that 10-[3-(2-naphthyl)phenyl]anthracene-9-boronic acid which had been synthesized by a known method was used instead of the 10-(2-naphthyl)anthracene-9-boronic acid. As a result of mass spectrometry, the resulting crystals were confirmed to be the compound 8. The compound 8 had an m/e value of 606 with respect to a molecular weight of 606.23.

Example 9

Compound 9 was synthesized according to the following synthesis scheme.

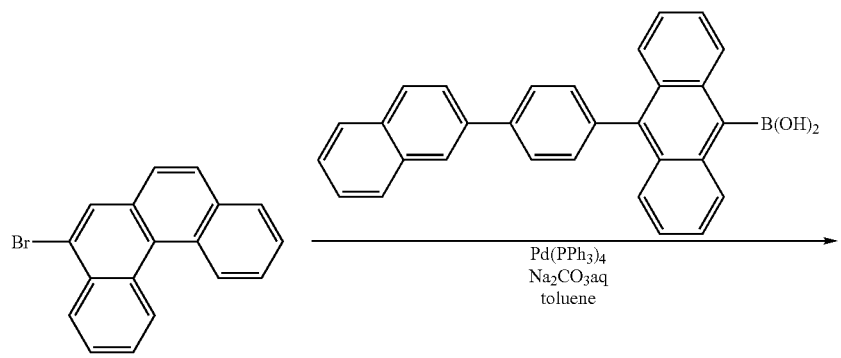

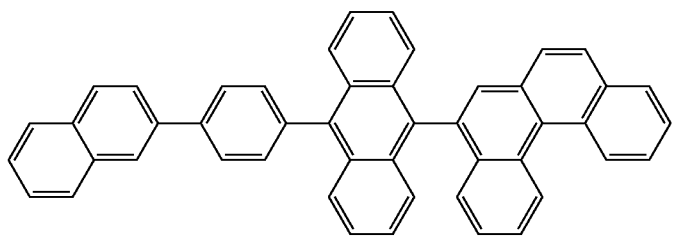

Compound 9

Crystals were synthesized and obtained in the same manner as in Example 1, except that 10-[4-(2-naphthyl)phenyl]anthracene-9-boronic acid which had been synthesized by a known method was used instead of the 10-(2-naphthyl)anthracene-9-boronic acid. As a result of mass spectrometry, the resulting crystals were confirmed to be the compound 9. The compound 9 had an m/e value of 606 with respect to a molecular weight of 606.23.

Example 10

Compound 10 was synthesized according to the following synthesis scheme.

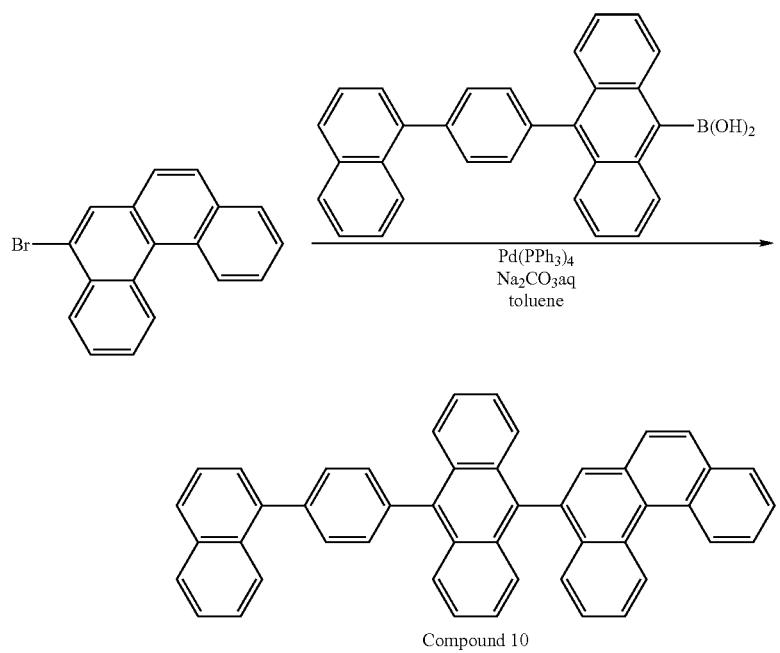

Compound 10

Crystals were synthesized and obtained in the same manner as in Example 1, except that 10-[4-(1-naphthyl)phenyl]anthracene-9-boronic acid which had been synthesized by a known method was used instead of the 10-(2-naphthyl)anthracene-9-boronic acid. As a result of mass spectrometry, the resulting crystals were confirmed to be the compound 10. The compound 10 had an m/e value of 606 with respect to a molecular weight of 606.23.

Synthesis Example 2

Synthesis of 5-(3-bromophenyl)benzo[c]phenanthrene 5-(3-bromophenyl)benzo[c]phenanthrene was synthesized according to the following synthesis scheme.

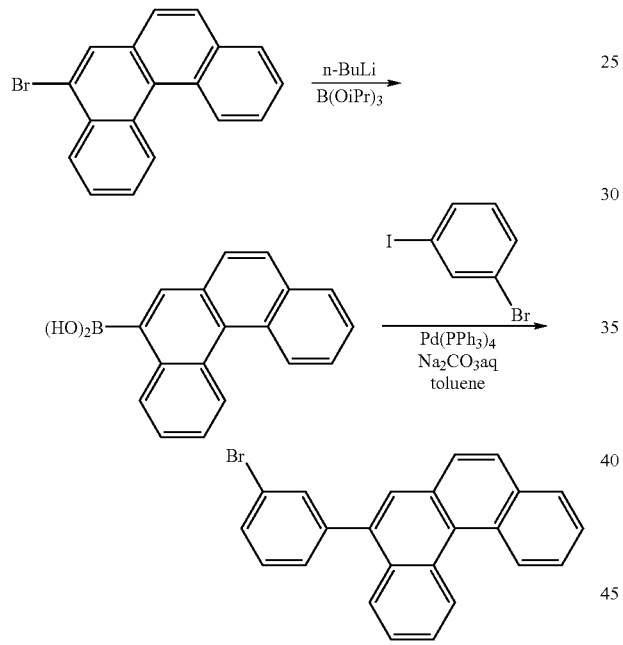

Under an argon atmosphere, 10.1 g of 5-bromobenzo[c]phenanthrene which had been prepared in Synthesis Example 1 was placed in a flask. 400 mL of dehydrated ether was added to this flask. The reaction solution was cooled to −40° C., and 22 ml of 1.6M hexane solution of n-butyllithium was added. The resultant was heated to 0° C., and stirred for an hour. The reaction solution was cooled to −60° C., and 10 mL of a dehydrated ether solution of 14.4 g of triisopropyl borate was dripped. The reaction solution was stirred for 5 hours while heating to room temperature. 100 mL of a 10% hydrochloric acid solution was added and the mixture was stirred for an hour. An aqueous phase was removed, and an organic phase which had been separated was washed with water and saturated brine, and then dried with magnesium sulfate. After the magnesium sulfate was filtered out, the organic phase was concentrated. The solids obtained were washed with hexane, whereby 5.37 g (yield: 60%) of benzo[c]phenanthrene-5-boronic acid was obtained.

Under an argon atmosphere, 3.26 g of the benzo[c]phenanthrene-5-boronic acid obtained, 2.83 g of 3-bromoiodobenzene, 0.231 g of tetrakis(triphenylphosphine)palladium(0), 40 mL of toluene and 20 mL of a 2M aqueous solution of sodium carbonate were placed in a flask. The resultant was refluxed with stirring for 8 hours. After cooling to room temperature, the reaction solution was extracted with toluene. An aqueous phase was removed and an organic phase which had been separated was washed with water and saturated brine sequentially, and then dried with magnesium sulfate. After the magnesium sulfate was filtered out, the organic phase was concentrated. The resulting residue was purified by means of silica gel column chromatography, whereby 3.64 g (yield: 95%) of 10-(3-bromophenyl)benzo[c]phenanthrene was obtained.

Example 11

Compound 11 was synthesized according to the following synthesis scheme.

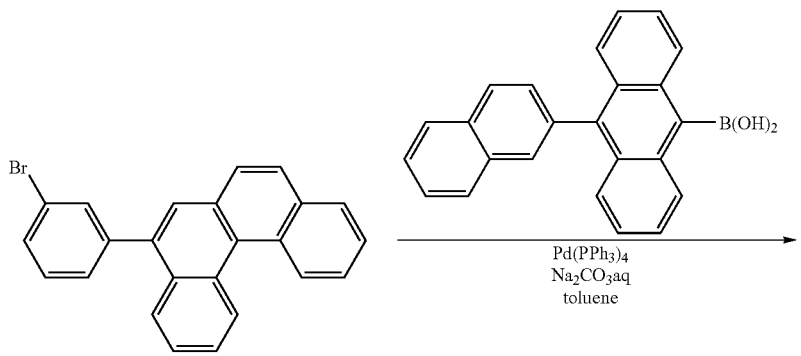

-continued

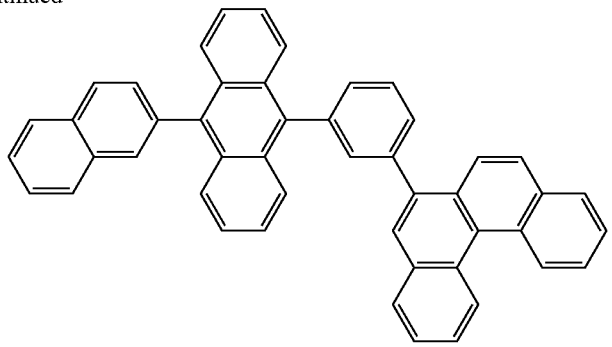
Compound 11

Crystals were synthesized and obtained in the same manner as in Example 1, except that 10-(3-bromophenyl)benzo[c]phenanthrene which had been prepared in Synthesis Example 2 was used instead of 5-bromobenzo[c]phenanthrene. As a result of mass spectrometry, the resulting crystals were confirmed to be the compound 11. The compound 11 had an m/e value of 606 with respect to a molecular weight of 606.23.

Example 12

Compound 12 was synthesized according to the following synthesis scheme.

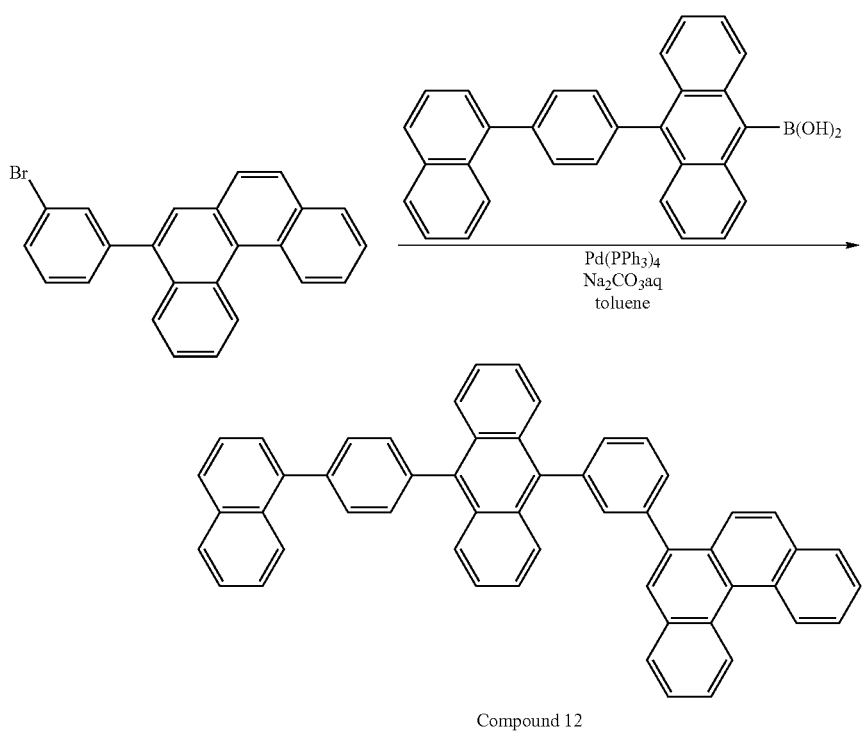
Compound 12

Crystals were synthesized and obtained in the same manner as in Example 11, except that 10-[4-(1-naphthyl)phenyl]anthracene-9-boronic acid which had been synthesized by a known method was used instead of the 10-(2-naphthyl)anthracene-9-boronic acid. As a result of mass spectrometry, the resulting crystals were confirmed to be the compound 12. The compound 12 had an m/e value of 682 with respect to a molecular weight of 682.27.

Example 13

Fabrication of Organic EL Device

A glass substrate of 25 mm by 75 mm by 1.1 mm thick with an ITO transparent electrode (anode) (GEOMATEC CO., LTD.) was subjected to ultrasonic cleaning with isopropyl alcohol for 5 minutes, and cleaned with ultraviolet rays and ozone for 30 minutes. The cleaned glass substrate with transparent electrode lines was mounted in a substrate holder of a vacuum vapor deposition apparatus. First, a 60 nm-thick film formed of compound A-1 (A-1 film) was formed on the surface where the transparent electrode lines were formed so as to cover the transparent electrode. Subsequently, on the A-1 film, a 20 nm-thick film formed of compound A-2 (A-2 film) was formed.

Subsequently, on the A-2 film, the compound 1 which had been prepared in Example 1 and arylamine derivative D-1 were formed into a 40 nm-thick film in a ratio by weight of 40:2. This film functioned as a blue emitting layer.

On the blue emitting layer, compound Alq was formed into a 20 nm-thick film by deposition. This film functioned as a electron-transporting layer. On this film, LiF was formed into a 1 nm-thick film. Then, metal Al was deposited on the LiF film in a 150 nm thickness to form a metal cathode, whereby an organic EL device was fabricated.

A-1

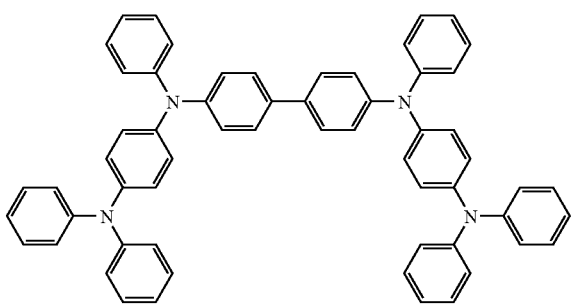

A-2

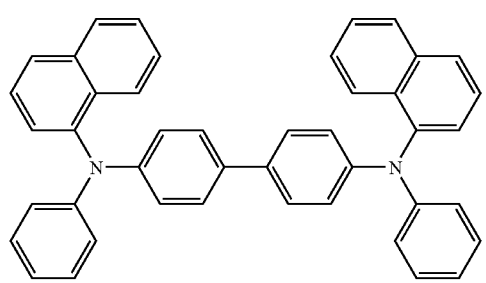

D-1

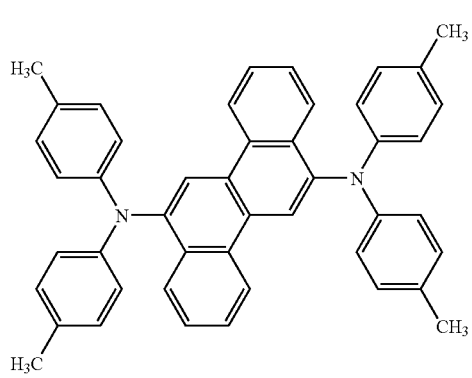

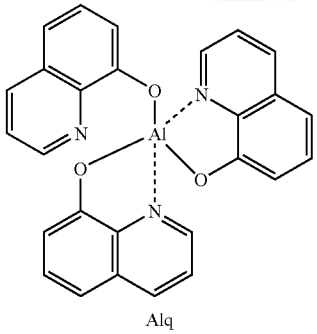

Alq

For the fabricated organic EL device, a luminous efficiency when driven at a current density of 10 mA/cm$^2$ and the half life of emission at the initial luminance of 1000 nit, room temperature and DC constant current driving were measured. The results are shown in Table 1.

Examples 14 to 24

Organic EL devices were fabricated and evaluated in the same manner as in Example 13, except that compounds in Table 1 were used as a host material instead of the compound 1. The results are shown in Table 1.

Comparative Example 1

An organic EL device was fabricated and evaluated in the same manner as in Example 13, except that compound B was used instead of the compound 1. The results are shown in Table 1.

Compound B

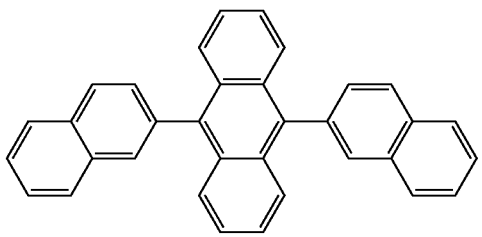

Comparative Example 2

An organic EL device was fabricated and evaluated in the same manner as in Example 13, except that compound C was used instead of the compound 1. The results are shown in Table 1.

Compound C

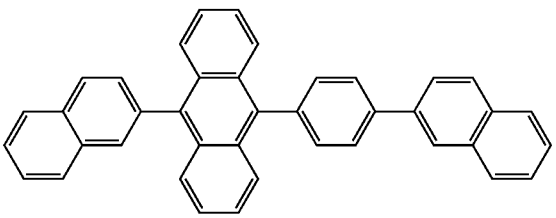

Comparative Example 3

An organic EL device was fabricated and evaluated in the same manner as in Example 13, except that compound D was used instead of the compound 1. The results are shown in Table 1.

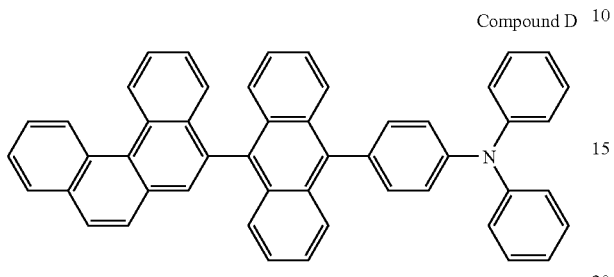

Compound D

TABLE 1

| | Host | Dopant | Luminous efficiency (cd/A) | Half life (hr) |
|---|---|---|---|---|
| Example 13 | Compound 1 | Compound D-1 | 6.5 | 7000 |
| Example 14 | Compound 2 | Compound D-1 | 6.5 | 7000 |
| Example 15 | Compound 3 | Compound D-1 | 6.7 | 7000 |
| Example 16 | Compound 4 | Compound D-1 | 6.7 | 7000 |
| Example 17 | Compound 5 | Compound D-1 | 6.7 | 7000 |
| Example 18 | Compound 6 | Compound D-1 | 6.7 | 7000 |
| Example 19 | Compound 7 | Compound D-1 | 6.7 | 8000 |
| Example 20 | Compound 8 | Compound D-1 | 6.7 | 8000 |
| Example 21 | Compound 9 | Compound D-1 | 6.7 | 8000 |
| Example 22 | Compound 10 | Compound D-1 | 6.7 | 8000 |
| Example 23 | Compound 11 | Compound D-1 | 7.2 | 8000 |
| Example 24 | Compound 12 | Compound D-1 | 7.2 | 8000 |
| Com. Ex. 1 | Compound B | Compound D-1 | 6.0 | 4000 |
| Com. Ex. 2 | Compound C | Compound D-1 | 6.4 | 5000 |
| Com. Ex. 3 | Compound D | Compound D-1 | 3.2 | 100 |

From Examples and Comparative Examples, it was confirmed that the organic EL device using the fused aromatic derivative of the invention had a long life and high efficiency. In particular, comparing Examples 13 to 24 to Comparative Example 3, it is found that the fused aromatic ring derivative of the invention has higher resistance to holes and electrons than the compound D containing an amino group, and is a very long-life material.

Example 25

Compound 13 was synthesized according to the following synthesis scheme.

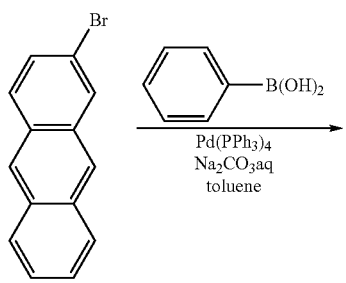

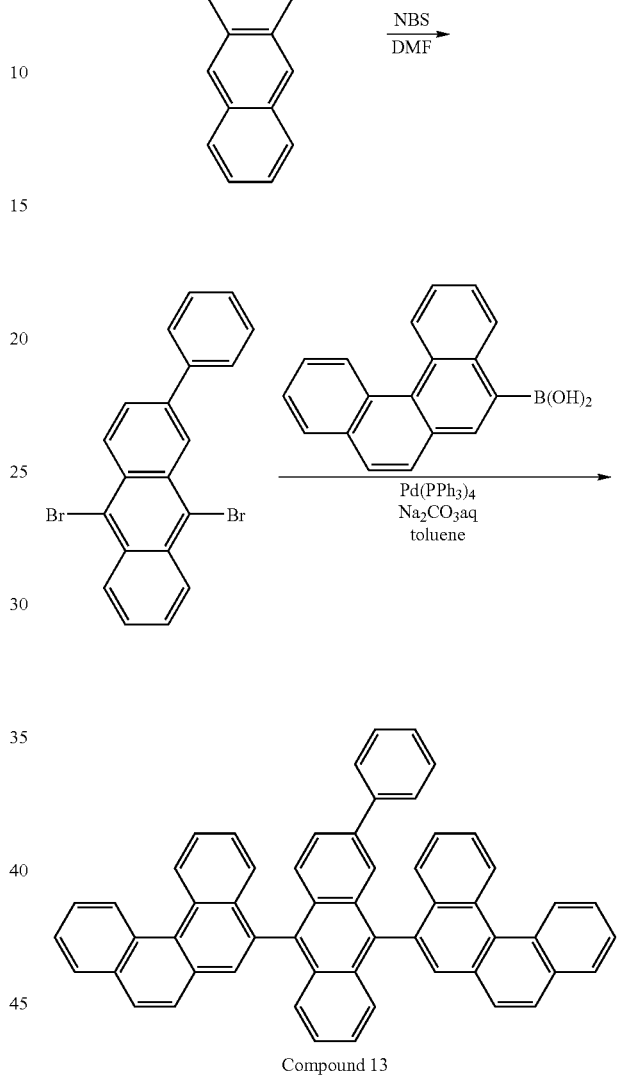

Compound 13

(1) Synthesis of phenylanthracene

Under an argon atmosphere, 14.5 g of phenylboronic acid, 25.7 g of 2-bromoanthracene, 4.62 g of tetrakis(triphenylphosphine)palladium(0), 400 mL of toluene and 200 mL of a 2M aqueous solution of sodium carbonate were charged, and the mixture was refluxed with stirring for 8 hours. After cooling to room temperature, deposited crystals were separated by filtration. The resulting solids were recrystallized with toluene-hexane and washed repeatedly, whereby 19.1 g (yield: 75%) of 2-phenylanthracene was obtained.

(2) Synthesis of 9,10-dibromo-2-phenylanthracene 19.1 g of 2-phenylanthracene was solved while heating in 200 mL of N,N-dimethylformamide. 20 mL of an N,N-dimethylformamide solution of 29.4 g of N-bromosuccinimide was added, and the mixture was heated with stirring at 60° C. for 6 hours. After cooling to room temperature, the reaction solution was poured into 1 L of water. The resulting solids were washed with methanol, water and methanol sequentially. Then, the washed solids were recrystallized with toluene-hexane and washed repeatedly, whereby 24.8 g (yield: 80%) of 9,10-dibromo-2-phenylanthracene was obtained.

(3) Synthesis of Compound 13

Under an argon atmosphere, 2.06 g of 9,10-dibromo-2-phenylanthracene, 2.52 g of benzo[c]phenanthrene-5-bronic acid, 0.231 g of tetrakis(triphenylphosphine)palladium(0), 40 mL of toluene and 20 mL of a 2M aqueous solution of sodium carbonate was charged, and the mixture was refluxed with stirring for 8 hours. After cooling to room temperature, deposited crystals was filtered out. The resulting solids were washed with methanol, water and methanol. Then, the washed solids were recrystallized with toluene, whereby 4.59 g of yellow crystals was obtained. As a result of mass spectrometry, the resulting crystals were confirmed to be the intended compound. The compound had an m/e value of 706 with respect to a molecular weight of 706.27.

Example 26

Compound 14 was synthesized according to the following synthesis scheme.

(1) Synthesis of 4-[benzo[c]phenanthrene-5-yl]phenylboronic acid

Under an argon atmosphere, 7.66 g of 10-(4-bromophenyl)benzo[c]phenanthrene was placed in a flask. 400 mL of dehydrated ether was added to the flask. The reaction solution was cooled to −40° C. Then 14 mL of a 1.6M hexane solution of n-butyllithium was added. After heating to 0° C., the solution was stirred for an hour. The reaction solution was cooled to −60° C. Then, 20 mL of a dehydrated ether solution in which 9.41 g of triisopropyl borate was solved was dripped. The reaction solution was stirred for five hours while heating to room temperature. 100 mL of a 10% hydrochloric acid solution was added and further stirred for an hour. An aqueous phase was removed, and an organic phase which had been separated was washed with water and saturated brine, and then dried with magnesium sulfate. After the magnesium sulfate was filtered out, the organic phase was concentrated. The resulting solids were washed with hexane, whereby 4.18 g (yield: 60%) of 4-[benzo[c]phenanthrene-5-yl]phenylboronic acid was obtained.

(2) Synthesis of Compound 14

Compound 14 was synthesized in the same manner as in Synthesis of the compound 13, except that 4-[benzo[c]phenanthrene-5-yl]phenylboronic acid was used instead of

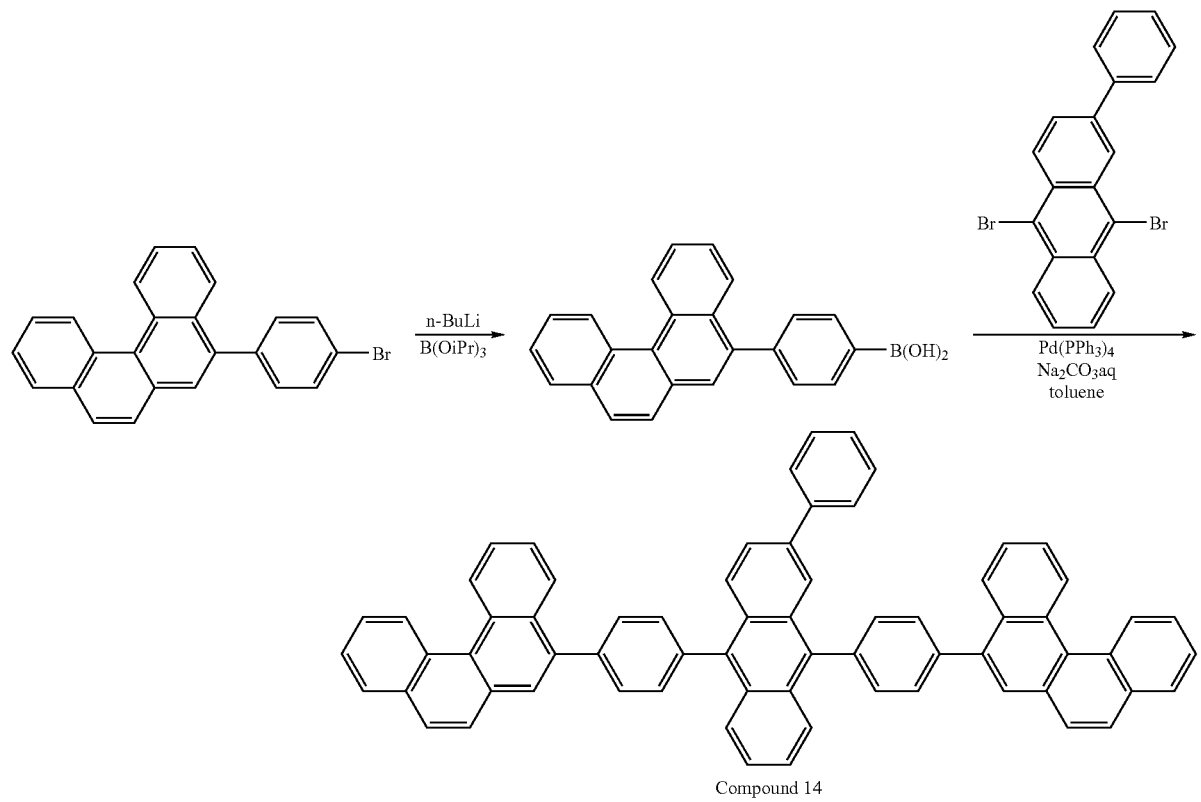

Compound 14 benzo[c]phenanthrene-5-boronic acid. As a result of mass spectrometry, the resulting compound was confirmed to be the intended compound. The compound had an m/e value of 858 with respect to a molecular weight of 858.33.

Example 27

Compound 15 was synthesized according to the following synthesis scheme.

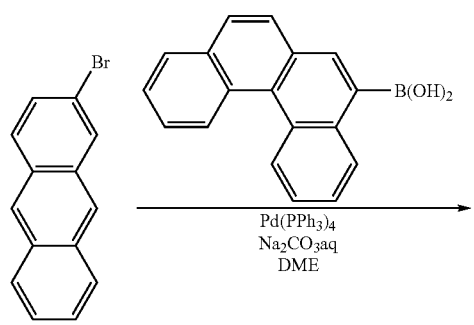

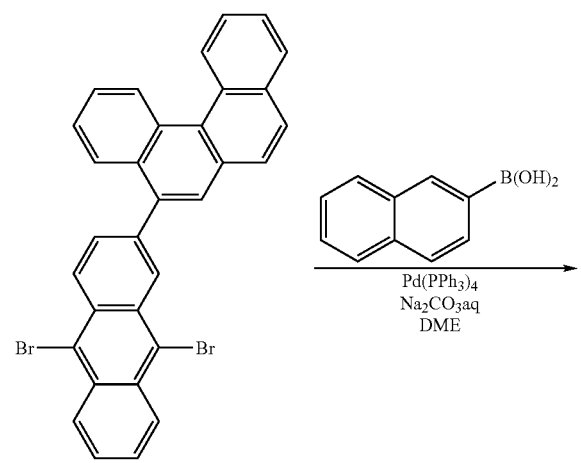

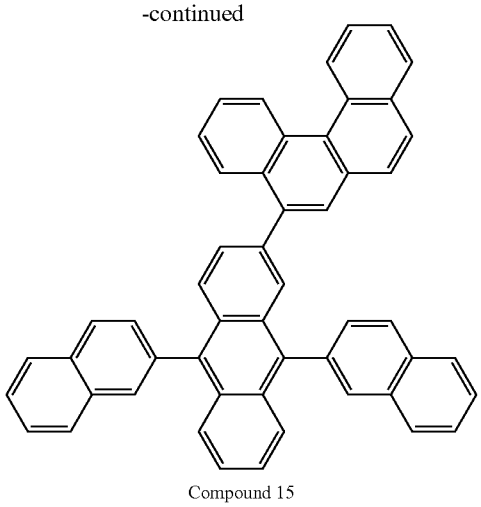

Compound 15

(1) Synthesis of 5-(2-anthryl)benzo[c]phenanthrene

Under an argon atmosphere, 5.98 g of benzo[c]phenanthrene-5-boronic acid, 5.14 g of 2-bromoanthracene, 0.462 g of tetrakis(triphenylphosphine)palladium(0), 30 mL of 1,2-dimethoxyethane and 15 mL of a 2M aqueous solution of sodium carbonate was charged, and the mixture was refluxed with stirring for 8 hours. After cooling to room temperature, deposited crystals were separated by filtration. The resulting solids were recrystallized with toluene-hexane and washed repeatedly, whereby 6.07 g (yield: 75%) of 5-(2-anthryl) benzo[c]phenanthrene was obtained.

(2) Synthesis of 5-(9,10-dibromoanthracene-2-yl) benzo[c]phenanthrene 6.07 g of 5-(2-anthryl)benzo[c]phenanthrene was solved while heating in 100 mL of N,N-dimethylformamide. 10 mL of an N,N-dimethylformamide solution of 5.87 g of N-bromosuccinimide was added and heated with stirring at 60° C. for 6 hours. After cooling to room temperature, the reaction solution was poured into 1 L of water. The resulting solids were washed with methanol, water and methanol sequentially. Then, the washed solids were recrystallized with toluene-hexane and washed repeatedly, whereby 6.75 g (yield: 80%) of 5-(9,10-dibromoanthracene-2-yl)benzo[c]phenanthrene was obtained.

(3) Synthesis of Compound 15

Under an argon atmosphere, 5.62 g of 5-(9,10-dibromoanthracene-2-yl)benzo[c]phenanthrene, 3.78 g of 2-naphthaleneboronic acid, 0.462 g of tetrakis(triphenylphosphine)palladium(0), 40 mL of toluene and 20 mL of a 2M aqueous solution of sodium carbonate were charged, and the mixture was refluxed with stirring for 8 hours. After cooling to room temperature, deposited crystals were filtered out. The resulting crystals were washed with methanol, water and methanol sequentially, and recrystallized with toluene, whereby 4.26 g of yellow crystals was obtained. As a result of mass spectrometry, the resulting crystals were confirmed to be the intended compound. The compound had an m/e value of 656 with respect to a molecular weight of 656.25.

Examples 28 to 30

Organic EL devices were fabricated in the same manner as in Example 13, except that compounds in Table 2 were used as a host instead of the compound 1, and the following compound D-2 was used as a dopant instead of the arylamine derivative D-1. Here, the ratio of the host and dopant was 40:2 (rate of film thickness). For the fabricated organic EL device, a device performance (driving voltage and luminous efficiency) when driven at a current density of 10 mA/cm$^2$ and the half life were measured. The results are shown in Table 2.

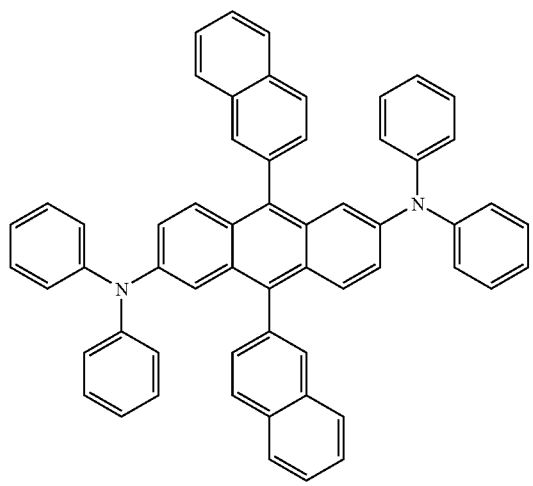

D-2

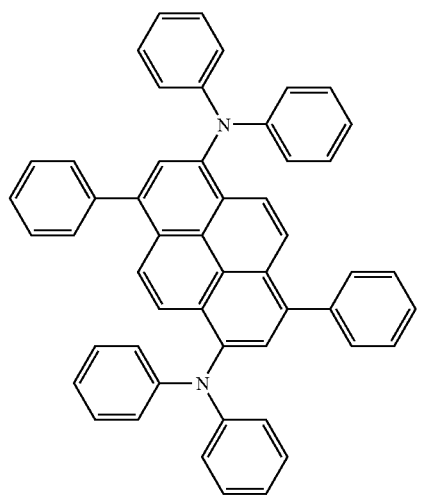

D-3

TABLE 2

| | Host | Dopant | Voltage (V) | Luminous efficiency (cd/A) | Light color | Life (hr) |
|---|---|---|---|---|---|---|
| Example 28 | Compound 13 | D-2 | 6.5 | 22 | green | 30000 |
| Example 29 | Compound 14 | D-2 | 6.6 | 22 | green | 30000 |
| Example 30 | Compound 15 | D-2 | 6.5 | 22 | green | 30000 |
| Example 31 | Compound 13 | D-3 | 6.7 | 21 | green | 50000 |
| Example 32 | Compound 14 | D-3 | 6.7 | 21 | green | 50000 |
| Example 33 | Compound 15 | D-3 | 6.7 | 21 | green | 50000 |
| Com. Ex. 4 | Compound B | D-2 | 7.0 | 17 | green | 10000 |

Examples 31 to 33

Organic EL devices were fabricated and evaluated in the same manner as in Example 13, except that compounds in Table 2 were used as a host instead of the compound 1, and the following compound D-3 was used as a dopant instead of the arylamine derivative D-1. Here, the ratio of the host and dopant was 40:2 (rate of film thickness). The results are shown in Table 2.

Comparative Example 4

An organic EL device was fabricated and evaluated in the same manner as in Example 13, except that the compound B was used as a host instead of the compound 1, and the compound D-2 was used as a dopant instead of the arylamine derivative D-1. Here, the ratio of the host and dopant was 40:2 (rate of film thickness). The results are shown in Table 2.

INDUSTRIAL APPLICABILITY

The fused aromatic ring derivative of the invention is preferable as a material for an organic EL device, in particular, as an emitting material.

The organic EL device of the invention can be suitably used as a light source such as a planar emitting body and backlight of a display, a display part of a portable phone, a PDA, a car navigator, or an instrument panel of an automobile, an illuminator, and the like.

The documents described in the specification are incorporated herein by reference in its entirety.

The invention claimed is:

1. A fused aromatic ring derivative shown by the following formula (1):

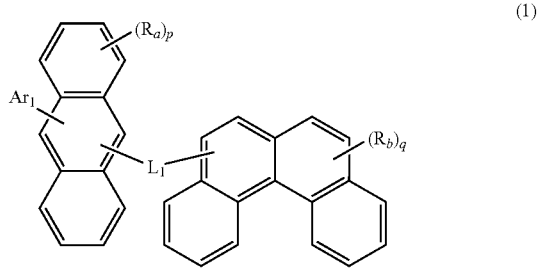

(1)

wherein $R_a$ and $R_b$ are independently a hydrogen atom or a substituent, p is an integer 1 to 8 and q is an integer of 1 to 11, when p is 2 or more, plural $R_a$s may be the same or different and adjacent $R_a$s may form a ring, when q is 2 or more, plural $R_b$s may be the same or different, L₁ is a single bond, or a substituted or unsubstituted divalent linking group, and Ar₁ is a substituted or unsubstituted aryl group and the aryl group is selected from the group consisting of a phenyl group, a naphthyl group, an anthryl group, a phenanthryl group, a naphthacenyl group, a pyrenyl group, a biphenyl group, a terphenyl group, and a benzophenathryl group, provided that the substituent of L₁, the substituent of Ar₁, R_a and R_b contain no substituted or unsubstituted amino group.

2. The fused aromatic ring derivative according to claim 1, which is shown by the following formula (2):

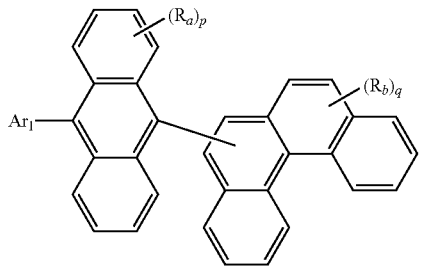

(2)

wherein $R_a$, $R_b$, $Ar_1$, p and q are the same as in the formula (1).

3. The fused aromatic ring derivative according to claim 1, wherein Ar₁ is a substituted or unsubstituted aryl group and the aryl group is selected from the group consisting of a naphthyl group, a phenanthryl group and a pyrenyl group.

4. The fused aromatic ring derivative according to claim 1, which is shown by the following formula (3):

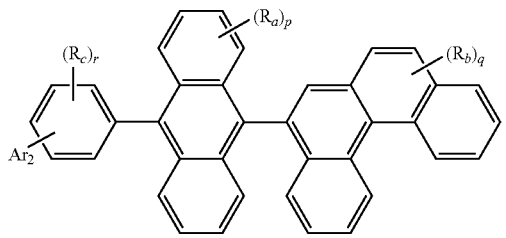

(3)

wherein $R_a$, $R_b$, p and q are the same as in the formula (1), $R_c$ is a halogen atom or a substituent, r is an integer of 1 to 4, when r is 2 or more, plural $R_c$s may be the same or different and adjacent $R_c$s may form a ring, and Ar₂ is a substituted or unsubstituted aryl group having 6 to 50 ring carbon atoms, provided that the substituent of Ar₂ and R_c contain no substituted or unsubstituted amino group.

5. The fused aromatic ring derivative according to claim 4, wherein Ar₂ is a substituted or unsubstituted fused aromatic ring group having 10 to 20 ring carbon atoms.

6. The fused aromatic ring derivative according to claim 1, which is shown by the following formula (4):

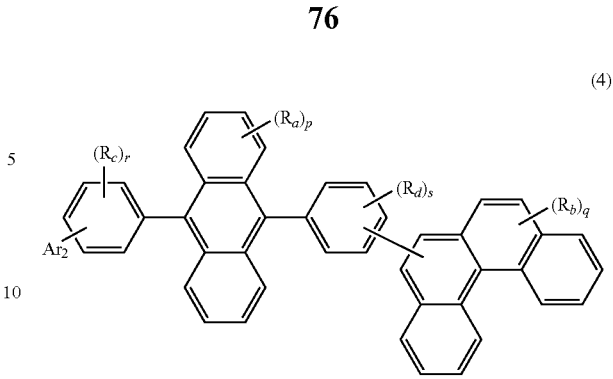

(4)

wherein $R_a$, $R_b$, p and q are the same as in the formula (1), $R_c$ and $R_d$ are independently a hydrogen atom or a substituent, r is an integer of 1 to 4 and s is an integer of 1 to 4, when r is two or more, plural $R_c$s may be the same or different, when s is two or more, plural $R_d$s may be the same or different, and Ar₂ is a substituted or unsubstituted aryl group having 6 to 50 ring carbon atoms, provided that the substituent of Ar₂, R_c and R_d contain no substituted or unsubstituted amino group.

7. The fused aromatic ring derivative according to claim 6, wherein Ar₂ is a substituted or unsubstituted fused aromatic ring group having 10 to 20 ring carbon atoms.

8. The fused aromatic ring derivative according to claim 1, which is shown by the following formula (5):

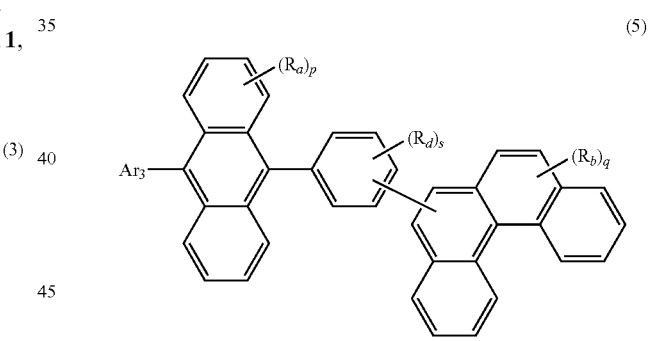

(5)

wherein $R_a$, $R_b$, p and q are the same as in the formula (1), $R_d$ is a hydrogen atom or a substituent, s is an integer of 1 to 4, when s is two or more, plural $R_d$s may be the same or different, and Ar₃ is a substituted or unsubstituted fused aromatic ring group and the fused aromatic ring group is selected from a group consisting of a naphthyl group, an anthryl group, a phenanthryl group, a naphthacenyl group, a pyrenyl group, and a benzophenathryl group, provided that the substituent of Ar₃ and R_d contain no substituted or unsubstituted amino group.

9. The fused aromatic ring derivative according to claim 8, wherein Ar₃ is a substituted or unsubstituted naphthyl group.

10. A material for an organic electroluminescence device comprising the fused aromatic ring derivative according to claim 1.

11. The material for an organic electroluminescence device according to claim 10, which is an emitting material.

12. An organic electroluminescence device comprising:
an anode, a cathode, and
one or more organic thin film layers comprising an emitting layer between the anode and the cathode,
wherein at least one of the organic thin film layers comprises the fused aromatic ring derivative according to claim 1.

13. The organic electroluminescence device according to claim 12, wherein the emitting layer comprises the fused aromatic ring derivative.

14. The organic electroluminescence device according to claim 13, wherein the fused aromatic ring derivative is a host material.

15. The organic electroluminescence device according to claim 12, wherein the emitting layer further comprises one selected from the group consisting of a fluorescent dopant and a phosphorescent dopant.

16. The organic electroluminescence device according to claim 15, wherein the fluorescent dopant is an aryl amine compound.

17. The organic electroluminescence device according to claim 15, wherein the fluorescent dopant is a styryl amine compound.

18. The fused aromatic ring derivative according to claim 1, wherein $L_1$ is a single bond, a substituted or unsubstituted phenylene group, a substituted or unsubstituted naphthacenylene group, a substituted or unsubstituted anthracenylene group, a substituted or unsubstituted pyrenylene group, a substituted or unsubstituted biphenylene group, a substituted or unsubstituted terphenylene group, a substituted or unsubstituted fluorenylene group, or a substituted or unsubstituted pyridylene group.

* * * * *